(12) United States Patent
Huang et al.

(10) Patent No.: US 8,013,141 B2
(45) Date of Patent: Sep. 6, 2011

(54) PROMOTER WITH HIGH EXPRESSION STRENGTH AND OVER-EXPRESSION IN VARIOUS TISSUES OF PLANT, AS WELL AS APPLICATION THEREOF

(75) Inventors: Pung-Ling Huang, Taipei (TW); Yi-Yin Do, Taipei (TW); Wei-Fen Huang, Taipei County (TW); Wei-Hsiang Lee, Taipei County (TW); Yung-Chen Lin, Taipei (TW)

(73) Assignee: National Taiwan University, Taipei (TW)

( * ) Notice: Subject to any disclaimer, the term of this patent is extended or adjusted under 35 U.S.C. 154(b) by 399 days.

(21) Appl. No.: 12/258,202

(22) Filed: Oct. 24, 2008

(65) Prior Publication Data

US 2011/0035845 A1   Feb. 10, 2011

(51) Int. Cl.
  *C12N 15/82* (2006.01)
  *C12N 15/63* (2006.01)
  *C07H 21/04* (2006.01)
  *A01H 5/00* (2006.01)

(52) U.S. Cl. ... 536/24.1; 536/23.1; 800/278; 435/320.1; 435/468

(58) Field of Classification Search .................. None
See application file for complete search history.

(56) References Cited

OTHER PUBLICATIONS

Christensen et al.; "Maize polyubiquitin genes: structure, thermal perturbation of expression and transcript splicing and promoter activity following transfer to protoplasts by electroporation"; Plant Molecular Biology 18: 675-689, 1992.
McElroy et al.; "Construction of expression vectors based on the rice actin 1 (Actl) 5' region for use in monocot transformation"; Mol Gen Genet (1991): 150-160.
Kawalleck et al.; "Polyubiquitin gene expression and structural properties of the ubi4-2 gene in Petroselinum crispum"; Plant Molecular Biology 21: 673-684, 1993.
Sun et al.; "A model for the evolution of polyubiquitin genes from the study of *Arabidopsis thaliana* ecotypes"; Plant Molecular Biology 34: 745-758, 1997.
Norris et al.; "The intron of *Arabidopsis thaliana* polyubiquitin genes is conserved in location and is a quantitative determinant of chimeric gene expression"; Plant Molecular Biology 21: 895-906, 1993.
Plesse et al.; "Effects of the polyubiquitin gene Ubi.U4 leader intron and first ubiquitin monomer on reporter gene expression in Nicotiana tabacum"; Plant Molecular Biology 45: 655-667, 2001.

*Primary Examiner* — Brent T Page
(74) *Attorney, Agent, or Firm* — Schmeiser, Olsen & Watts LLP

(57) ABSTRACT

The invention provides a promoter that has high expression strength and can be over-expressed in various tissues of plant, said promoter is a promoter for banana polyubiquitin (polyubiquitin) gene MhUBQ1, and has a sequence as SEQ ID No: 3. The invention provides further a gene expression cassette that contains a promoter comprising a DNA sequence as SEQ ID No: 3, and a polynucleotide having a open reading frame (ORF) linked to the 3' terminal of said promoter, wherein said promoter can activate the transcription of said polynucleotide in a organism containing said gene expression cassette. The invention provides further a gene expression vector that contains a promoter having a DNA sequence as SEQ ID No: 3. Also, the invention provides a process for producing a transgenic plant or part of organ, tissue or cell thereof containing the above-described gene expression cassette.

6 Claims, 12 Drawing Sheets

(6 of 12 Drawing Sheet(s) Filed in Color)

SEQUENCE LISTING

```
<160> NUMBER OF SEQ ID NOS: 11

<210> SEQ ID NO 1
<211> LENGTH: 3059
<212> TYPE: DNA
<213> ORGANISM: Arabidopsis thaliana
<220> FEATURE:
<221> NAME/KEY: gene
<222> LOCATION: (1)...(3059)
<300> PUBLICATION INFORMATION:
<308> DATABASE ACCESSION NUMBER: Genbank/ L05363
<309> DATABASE ENTRY DATE: 1995-08-03

<400> SEQUENCE: 1
aagcttcgga tttggagcca agtctcataa acgccattgt ggaagaaagt cttgagttgg      60
tggtaatgta acagagtagt aagaacagag aagagagaga gtgtgagata catgaattgt     120
cgggcaacaa aaatcctgaa catcttattt tagcaaagag aaagagttcc gagtctgtag     180
cagaagagtg aggagaaatt taagctcttg gacttgtgaa ttgttccgcc tcttgaatac     240
ttcttcaatc ctcatatatt cttcttctat gttacctgaa aaccggcatt taatctcgcg     300
ggtttattcc ggttcaacat tttttttgtt ttgagttatt atctgggctt aataacgcag     360
gcctgaaata aattcaaggc ccaactgttt ttttttttaa gaagttgctg ttaaaaaaaa     420
```

```
aaaaagggaa ttaacaacaa caacaaaaaa agataaagaa aataataaca attactttaa      480
ttgtagacta aaaaaacata gattttatca tgaaaaaaag agaaaagaaa taaaaacttg      540
gatcaaaaaa aaaaacatac agatcttcta attattaact tttcttaaaa attaggtcct     600
ttttcccaac aattaggttt agagttttgg aattaaacca aaaagattgt tctaaaaaat     660
actcaaattt ggtagataag tttccttatt ttaattagtc aatggtagat acttttttt      720 cttttcttta ttagagtaga ttagaatctt ttatgccaag tattgataaa ttaaatcaag    780
aagataaact atcataatca acatgaaatt aaaagaaaaa tctcatatat agtattagta    840
ttctctatat atattatgat tgcttattct taatggggttg ggttaaccaa gacatagtct   900
taatggaaag aatctttttt gaacttttc cttattgatt aaattcttct atagaaaaga     960
aagaaattat ttgaggaaaa gtatatacaa aaagaaaaat agaaaatgt cagtgaagca     1020 gatgtaatgg atgacctaat ccaaccacca ccataggatg tttctacttg agtcggtctt    1080
ttaaaaacgc acggtggaaa atagacacgt atcatatgat tccttccttt agtttcgtga    1140
taataatcct caactgatat cttccttttt ttgttttggc taaagatatt ttattctcat    1200
taatagaaaa gacggttttg ggcttttggt ttgcgatata aagaagacct tcgtgtggaa    1260
gataataatt catcctttcg tctttttctg actcttcaat ctctcccaaa gcctaaagcg    1320
atctctgcaa atctctcgcg actctctctt tcaaggtata ttttctgatt cttttgttt     1380 ttgattcgta tctgatctcc aattttgtt atgtggatta ttgaatcttt tgtataaatt     1440
gcttttgaca atattgttcg tttcgtcaat ccagcttcta aattttgtcc tgattactaa    1500
gatatcgatt cgtagtgttt acatctgtgt aatttcttgc ttgattgtga aattaggatt    1560
ttcaaggacg atctattcaa ttttttgtgtt tctttgttc gattctctct gttttaggtt     1620
tcttatgttt agatccgttt ctctttggtg ttgttttgat ttctcttacg gcttttgatt    1680
tggtatatgt tcgctgattg gtttctactt gttctattgt tttatttcag atgcaaatct    1740
tcgtgaaaac actcactggc aagactatca ctctcgaggt tgagagctct gacaccatcg    1800
acaatgttaa ggcaaagatt caggacaagg aaggcattcc tccggatcag caaagattaa    1860
tattcgccgg taaacagcta gaagatggcc gtaccttggc cgattacaac attcagaaag    1920
aatcaaccct tcatttggtt ctccgtttaa gaggtggtat gcaaatcttt gtcaagactc    1980
tgactggcaa gaccattact ttggaggttg agagctctga cactattgac aacgtcaaag    2040
caaagatcca ggacaaggaa ggaatccctc cggatcagca gagacttatc tttgccggta    2100
agcagcttga gacggaaga actcttgctg actacaacat tcaaaaggag tcgacccttc     2160
atttggtgct tcgtctcaga ggtggtatgc aaatctttgt caagaccctc actggtaaaa    2220
caatcaccct tgaggttgag agttcagaca ccattgacaa tgtcaaagct aagatccaag    2280
ataaagaggg aattcctccg gatcagcaga ggcttatctt tgccggtaag cagctcgaag    2340
atggacgcac ccttgcagat tacaacatcc aaaaggagtc gacacttcat cttgtgcttc    2400
gtctccgtgg tggtatgcag atctttgtga agacccttac cggaaagacc attactctgg    2460
aggttgaaag ctcagacacc atcgataatg tcaaggctaa gattcaggac aaggaaggga    2520
tcccaccaga ccaacagaga ctcatcttcg ctggaaaaca gcttgaggat ggtcgcacac    2580
ttgcagatta caacatccag aaggagtcga ctcttcactt ggttcttcgt cttcgtggtg    2640
gaagcttcta agcttttttgt gatctgatga taagtggttg gttcgtgtct catgcacttg    2700
ggaggtgatc tatttcacct ggtgtagttt gtgtttccgt cagttggaaa aacttatccc    2760
tatcgatttc gttttcattt tctgcttttc ttttatgtac cttcgtttgg gcttgtaacg    2820
```

-continued

```
ggcctttgta tttcaactct caataataat ccaagtgcat gttaaacaat ttgtcatctg   2880
tttcggcttt gatatactac tggtgaagat gggccgtact actgcatcac aacgaaaaat   2940
aataataaga tgaaaaactt gaagtggaaa aaaaaaaaaa cttgaatgtt cactactact   3000
catgaccata atgtttaaca tacatagctc aataagtatt tttgtgaata tggccaaca    3059
```

<210> SEQ ID NO 2
<211> LENGTH: 1146
<212> TYPE: DNA
<213> ORGANISM: Banana
<220> FEATURE:
<221> NAME/KEY: CDS
<222> LOCATION: (1)..(1146)
<223> OTHER INFORMATION: Musa spp. cv. Hsien Jin Chiao (AAA group)
<300> PUBLICATION INFORMATION:
<308> DATABASE ACCESSION NUMBER: Genbank/ AF502575
<309> DATABASE ENTRY DATE: 2005-12-31

<400> SEQUENCE: 2

```
atgcagatct tgttaaaaac tctcactggc aagaccatca cccttgaggt tgaatcctct     60
gacaccatcg acaatgtcaa ggctaagatc caggacaaag agggaatccc tccagaccag    120
caaaggctga tctttgccgg taagcaactt gaggatggcc ggaccctttgc ggattacaac   180 atccagaagg agtccaccct ccacctcgta cttcgccttc gtggtggcat gcaaatcttt    240
gtcaagacct tgactggcaa gaccatcacc ctcgaggtgg agagttctga caccatcgac    300
aatgtcaagg ctaagattca ggataaggag ggcattcctc cagaccagca aaggctcatc    360
tttgccggca agcagcttga ggatggccgc accctggctg attacaacat ccagaaggag    420
tccaccctcc accttgtgct tcgacttcgg ggtggcatgc aaatctttgt caagaccttg    480
actggcaaga ccatcaccct cgaggtggag agttctgaca ccatcgacaa tgtcaaggcc    540
aagattcagg ataaggaggg cattccaccg gaccagcaga ggctcatctt tgccggcaag    600
cagctggagg acgccgcac cttggctgat acaacatcc agaaggagtc cacccctccac    660 cttgtcctcc gcctccgtgg tggcatgcaa atcttcgtca agactttgac tgggaagacc    720 atcacccttta aggtggagag ctcggacacc atcgacaatg taaaggccaa gattcaggac    780
aaggagggta ttcccccgga ccagcaaagg ctcatctttg ccggcaagca gcttgaggat    840
ggccgcaccc tggcagatta caacattcag aaggagtcta cccttcacct tgtgctgaga    900
cttaggggtg gcatgcagat cttttgttaag acgcttacag ggaagaccat taccttggag    960
gtggagagct cggacacgat tgataatgtc aaggcaaaga tccaggacaa ggagggggatt   1020 ccaccggatc agcagaggct gatctttgct gggaagcagc tggaggacgg cgcacccctg    1080
gcagattaca cattcagaa ggaatccacc cttcacctgg tgctccgcct ccgcgggggt     1140
cattaa                                                                1146
```

<210> SEQ ID NO 3
<211> LENGTH: 3093
<212> TYPE: DNA
<213> ORGANISM: Banana
<220> FEATURE:
<223> OTHER INFORMATION: Musa spp. cv. Hsien Jin Chiao (AAA group)

<400> SEQUENCE: 3

```
ggatccacat gttctgcaga tagatagata ccatcttctg aggcttttttg tagttccaag     60 ttgtaggcta attctcggtt cttccaagaa aatatgatga acactcacta attctttcta    120
ccctgtccac catgcaggtt tagcttctca acaatgtttt tcgcacatag taagtgagat    180
tcacgatacg tctgatacaa tttaaacaac catttcctaa ttattggtac aaattagctc    240
```

```
caacatacat ttacgagttt ttgtgtgtga aaattgtgca ggggagaaca cagtcagtac    300
gctcgggcga ttcgtgttga tagtatggat gttcgtagtc ctaattatca actcgagcta    360
cacagccagc ttgacgtcaa tcctcacagt tcaacagctc tcatcaggga ttactgggct    420
tgacagcttg ctctcgtcct ctgaacctat tggctaccag aaggggaagt tttcgaggaa    480
ttacatgata gaaagctcca acattcctgc gtccagactc gtacctctga actcccctgc    540
agagtatgct agggctctcc ggctggggcc aaagggtggt ggtgtggcag ccatcgtcga    600
tgagattcca tacgtcgaga tcttcttgtc tgcctactgc cagttcaaga tcgtgggtca    660
agagttcacc aaaaatggat ggggatttgt aagtatctcg atccaagaat gcaagcatcg    720
ttaccctctg ttaacatcaa cacatcttta tggtaacagc agctcaggat tcattggcac    780
tcgaagcatt actctttttct tttaagagca attccagtat catttgaact gttttcttca    840
tttcagattc tcttagagat tcagaattga tagacaacaa aaagtcttag caagtcttca    900
ttgttatatg gctacgaaga cgaacaaaca aacatgacaa gtgcaaataa tgaactccca    960
agcaaatctc tatcatcttc ttgtgtgaaa agtgaagctt tacattacga caatagtcga   1020
gatgtgaacc tctactcgat atttctgaag gctactttca tgaaataagt tcaaccaaga   1080
atcgattagt acgatgtagt cagtctgtca tgcaatatcc tttgtgcgga tacagttttg   1140
tcgaatctat agaattttaa tgtggacttc aattttcatt ctccgacagg cattccagag   1200
ggactctcct cttgcggttg acctgtccac tgcaatcctg gcactatccg agaatggcga   1260
tctccagacg atccacgaga aatggttgtc gcgtgctgga tgtccttccc aaggtgttga   1320
agaagaagcg aaccggctaa gtctcagtag cttctggggt ctcttcctcc tcagtggcat   1380
cgtgtgtttt cttgctctca tccttttctg cataaaggtg tgctatcagt atgccatgta   1440
cagcagcgca gaggtcgaca agcccagaga aaacgacttg atcgacggaa gccaacatgc   1500
cctatgcaag ttaaagagca tcaaggcttt gattcgcttc ttcgacatga aggaagaaga   1560
aatcaacaaa gtcatcacga aaaaaccgag tggtacacaa aatggtcctc caacttcgga   1620
tgatgggcat tcgctgccat cttcatagaa cgtggtaaga agatgcagaa atcttttctta   1680 ccaaaagaac atcagctatt ttgcattagg aaatgcgatt acttggtaga cttgatgaag   1740
actgcgactg cgactgtttc acaaagtgcg agttcttaat ttgtcttgaa tctcttataa   1800
agcaatccag aacatacata ttttctagtg ctggatgtaa ctcgatatgt agctgcaaca   1860
aaatcaaagg aaatttaagc tgcacaaaag atgatcgtct tcttttgatg aaagaatga    1920 gcatatcgtg gaatcgctac gtcgtctctt cttaccgctg ccatcaccaa ggatcgcagg   1980
taaatgagac acttctctta catcccacgc ggatacccaa ctagtccagg agggatagga   2040
ggaggactga acttgctggg tcccacatga ggttttgtcc gatcgccaaa tcaactgggc   2100
ccacagctgt ggcatccgag atggaagcct gacgcctgtc aagggcacgt gcatgtgatt   2160
tcttctgcgt gcggtcacct ctggcgtact cgggaaaaat ctggcaacgg acgaattcct   2220
tctcgaatgc aacgccgtta tctttgaacg gcacccgtgc cacgagagag taatgctcgc   2280
ctcacctacc agcttgctgg ttggcgaagc aacatggaac ccacgcgtga gtcatgaact   2340
gtaatgtggg aataggacgg atacacgtta ctccgacagc gacgtcctac cttgcggtag   2400
caggatacgt ctcttatatc gtccgtccac ttgtgcggcg atcactggct gaactctttt   2460
taggtaacat caccggtagg taatctcacg ccagaagatg gctataaata aggctcctca   2520
ggcccgatct caatgcgctc tattcaatat tgtcgaaagg cttgcaagtt tcttcctttt   2580
gcttcaaggt atgttttcgc ctataccctga gtatttccct attttaggcc ttttttgcct   2640
```

```
ttttattt  tatttctgt  agcttcgatg  ttaatggatg  aagggtaga  tcaatcgttt    2700 tctttctatt  ttattgatgt  tgttgttaac  aattgtctga  ttctttgccg  actcctttga   2760
gagatttggt  aatcgttgc   gattttcttt  tttgtgatat  gttagttggt  ctataaaagt   2820
cgattcttat  attgttgtga  cacgatctac  cacgtcttgc  atatgttttc  ttgtaggaag   2880
cttcgtctca  gatttgaagc  atattgatgt  gtcgcttttg  atcatttagt  cgaagtggtt   2940
gattttaatt  ttaggtcatt  cattttttt   cttgtacact  ttgcatgatc  cgtctcagat   3000
ctgatcaatt  gttgttagtc  cagtagtcct  ttttgtgta   ttagatctga  tggttgtttt   3060
ctgactcctt  tcttcttta   tctctttgat  cag                                 3093

<210> SEQ ID NO 4
<211> LENGTH: 18
<212> TYPE: DNA
<213> ORGANISM: artificial sequence
<220> FEATURE:
<223> OTHER INFORMATION: forward primer

<400> SEQUENCE: 4
tgcatgcatg caagcttg                                                     18

<210> SEQ ID NO 5
<211> LENGTH: 37
<212> TYPE: DNA
<213> ORGANISM: artificial sequence
<220> FEATURE:
<223> OTHER INFORMATION: reverse primer

<400> SEQUENCE: 5
ataccatggc ccggggatcc tctagagtcg aggtcct                                37

<210> SEQ ID NO 6
<211> LENGTH: 21
<212> TYPE: DNA
<213> ORGANISM: artificial sequence
<220> FEATURE:
<223> OTHER INFORMATION: forward primer

<400> SEQUENCE: 6
ataccatggt acgtcctgta g                                                 21

<210> SEQ ID NO 7
<211> LENGTH: 22
<212> TYPE: DNA
<213> ORGANISM: artificial sequence
<220> FEATURE:
<223> OTHER INFORMATION: reverse primer

<400> SEQUENCE: 7
acggccagtg ccaagcttgc at                                                22

<210> SEQ ID NO 8
<211> LENGTH: 21
<212> TYPE: DNA
<213> ORGANISM: artificial sequence
<220> FEATURE:
<223> OTHER INFORMATION: forward primer

<400> SEQUENCE: 8
atggtacgtc ctgtagaaac c                                                 21

<210> SEQ ID NO 9
<211> LENGTH: 22
```

-continued

```
<212> TYPE: DNA
<213> ORGANISM: artificial sequence
<220> FEATURE:
<223> OTHER INFORMATION: reverse primer

<400> SEQUENCE: 9
tgatacgtac acttttcccg gc                                              22

<210> SEQ ID NO 10
<211> LENGTH: 27
<212> TYPE: DNA
<213> ORGANISM: artificial sequence
<220> FEATURE:
<223> OTHER INFORMATION: forward primer

<400> SEQUENCE: 10
ggatccacat gttctgcaga tagatag                                         27

<210> SEQ ID NO 11
<211> LENGTH: 27
<212> TYPE: DNA
<213> ORGANISM: artificial sequence
<220> FEATURE:
<223> OTHER INFORMATION: reverse primer

<400> SEQUENCE: 11
ctgatcaaag agataaaaga agaaagg                                         27
```

PROMOTER WITH HIGH EXPRESSION STRENGTH AND OVER-EXPRESSION IN VARIOUS TISSUES OF PLANT, AS WELL AS APPLICATION THEREOF

BACKGROUND OF THE INVENTION

1. Field of the Invention

The invention relates to a gene promoter characterized in that it can be over-expressed in various plant tissues, as well as to applications of said promoter.

2. Description of the Prior Art

Banana (*Musa* spp.) belongs to Musaceae, Monocotyledon, with its fruit being fragrant and delicious, as well as having high nutritional value. The desired banana protein can be used to produce in large quantities vaccines useful for treating diseases in humans or animals, by using the banana as gene transfer material. The banana can be used to directly uptake the vaccine orally, which is not only more convenient and safer than a vaccine injection, but also prevents proteins from losing their function through denaturizing in cooking, since banana fruit can be eaten raw.

In order to enable a transgenic plant to produce protein in large amounts, in the construction of a gene transfer construct selection of a proper promoter for activating the target gene that is highly associated with the production of proteins is important. At present, most conventional technologies for plant gene transfer has use cauliflower mosaic virus 35S (CaMV 35S) promoter to induce the over-expression of target genes in dicotyledon or monocotyledon plants. However, the expression of CaMV 35S promoter in a monocotyledon plant is relatively low. In order to improve the activation ability of a promoter, cloning of a promoter with high expression strength originally present in the monocotyledon plant, such as the Act1 promoter for paddy rice actin gene, Ubi1 promoter for corn polyubiquitin gene, and the like, might be carried out. Among these, the expression strength of Ubi1 promoter in a monocotyledon plant system is higher and more stable than that of CaMV 35S promoter, thereby the gene expression can be increased significantly (Christensen et al., 1992; McElroy et al., 1991).

Ubiquitin is a small molecular protein extensively present in a eukaryote. Its gene belongs to a polygene family. Based on its gene structure, it can be classified into three major groups: polyubiquitin gene, ubiquitin extension gene and ubiquitin-like gene. Polyubiquitin gene consists of arranging identical mono ubiquitin gene head-to-tail in a manner of tandem repeat in same direction. There are many types of polyubiquitin gene in plants, each with different modulation mechanisms. Further, there are different expression patterns such as constitutive expression, inducible expression, tissue specific expression and the like. Polyubiquitin gene with constitutive expression can be over-expressed in all tissues and organs, such as parsley ubi 4-2 (Kawalleck et al., 1993) and UBQ10 of *Arabidopsis thialana* (Sun et al., 1997) and the like.

Another feature of polyubiquitin gene is that there is a first intron connected tightly with ATG at its 5'-untranslation region, where the sequence at the joint of this intron and exon is highly conserved, which is consistent with AG/gt principle at 5'-terminal cleavage and the ag/GT principle at 3'-terminal cleavage, such as genes of rice RUBQ1 and 2, sunflower UbB1 and 2 as well as *Arabidopsis thialana* UBQ3, 10 and 11. The presence or absence of the first intron might influence the activity of a polyubiquitin gene promoter, and its length varies with species (Norris et al., 1993; Plesse et al., 2001).

Many researches had shown that ubiquitin gene promoters isolated from a variety of plants exhibited expression activity in gene transfer system stronger than that of CaMV 35S promoter. Accordingly, studies on the activity and tissue-specific expression of ubiquitin gene promoter in order to assess its applications will become a topic worthy of future investigation.

In view of the importance of developing promoters with high activating ability for the biotechnical industry, the inventor had thought to improve and innovate, and finally, after studying intensively for many years, successfully developed the promoter with high expression strength and capable of being over-expressed in various tissues of a plant, as well as its application according to the invention.

SUMMARY OF THE INVENTION

One object of the invention is to provide a promoter characterized in that it exhibits high expression strength and can be over-expressed in various tissues of a plant.

Another object of the invention is to provide an application of the promoter that has high expression strength and can be over-expressed in various tissues of a plant, where by taking advantage of the high ability of activating a downstream gene; the promoter can be used for over-expression of a target gene in various tissues of a plant.

Yet another object of the invention is to provide a gene expression vector. Said vector comprises a promoter with high expression strength and can be over-expressed in various tissues of a plant, such that, by cloning a target gene into a plant cell through said vector, said target gene can be over-expressed in various tissues of said plant.

A promoter with high expression strength and can be over-expressed in various tissues of a plant that can achieve the above-described objectives of the invention is characterized in that sequences of said promoter are obtained from genomic DNA of banana (*Musa* spp.). By using a fragment of *Arabidopsis thialana* polyubiquitin UBQ3 gene (GenBank accession number L05363; SEQ ID No: 1) as a probe, selection of banana genomic library is carried out, and after several purifications, a banana polyubiquitin genomic clone is obtained. By performing restriction map analysis and nucleic acid sequencing, a banana polyubiquitin gene Mh-UBQ1 is obtained, with its coding region sequence having a GenBank accession number as AF502575 (SEQ ID No: 2), and a 3,093 bp regional sequence (SEQ ID No: 3) ahead of the translation start site (gene code ATG) of banana polyubiquitin gene Mh-UBQ1 is also obtained, wherein said 3,093 bp regional sequence is at 5'upstream region of the translation start site (ATG); wherein said 5'upstream region comprises the postulated gene promoter, 5'-end untranslated region (5'UTR), an postulated exon 1 and intron 1; and wherein said 3,093 bp DNA sequence is used as the banana polyubiquitin gene Mh-UBQ1 promoter in the construction of cloning vector.

To analyze the ability of said banana polyubiquitin gene Mh-UBQ1 promoter (SEQ ID No: 3) for activating a downstream gene, said promoter sequence is ligated to the 5' terminal of the gene sequence of a reporter gene, β-glucuronidase (GUS), to act as the promoter of said reporter gene, and then Mh-UBQ1 promoter is constructed into a *Agrobacterium tumefaciens* cloning vector to form a pMhUBQ1p-GUS plasmid; next, by means of *Agrobacterium tumefaciens* transformation, said pMhUBQ1p-GUS plasmid is cloned into model plants, *Arabidopsis thialana* ecotype Columbia and *Nicotiana tabacum* L., respectively; and finally, the activity of said promoter is assayed by GUS histochemical staining. The results show that said banana polyubiquitin gene Mh-UBQ1 promoter (SEQ ID No: 3) driven target gene to over-express in all tissues of a plant. Accordingly, the inventive banana polyubiquitin gene Mh-UBQ1 promoter (SEQ ID No: 3) possesses activating ability of high expression strength, and can be over-expressed in various tissues of a plant.

In addition to providing a promoter that has a high expression strength and can be over-expressed in various tissues of a plant, the invention provides further a gene expression cassette. Said gene expression cassette comprises: (1) the inventive promoter sequence (SEQ ID No: 3), and (2) a length of polynucleotide having an open reading frame (ORF), i.e. a target gene; wherein said polynucleotide is ligated to the 3' terminal of the inventive promoter, and said promoter can initiate the transcription of said polynucleotide in a organism containing said gene expression cassette. In a preferred embodiment, said target gene is a reporter gene β-glucuronidase (GUS).

Further, the inventive banana polyubiquitin gene Mh-UBQ 1 promoter (SEQ ID No: 3) can be constructed into a commercial cloning vector which includes, but not limited to: pBI101, pBI121, pBIN19 (ClonTech), pCAMBIA1301, pCAMBIA1305, pGREEN (GenBank Accession No: AJ007829), pGREEN II (GenBank Accession No: EF590266) (www.pGreen.ac.uk), pGreen0029 (John Innes Centre), to form a gene expression vector. Then, a target gene can be inserted said gene expression vector in a manner that, after inserting said target gene to the 3' terminal of the inventive promoter, a gene expression cassette described above is formed. Furthermore, the inventive promoter together with the target gene ligated at its 3' terminal can be transferred in a target plant through gene transfer, and hence change further the genomic constitution of the transgenic plant such that the inventive promoter with the target gene can activate effectively the expression of said target gene in the objective transgenic plant and the progeny thereof.

Moreover, the invention provides a process for producing a transgenic plant or part of organ, tissue or cell thereof containing the above-described gene expression cassette, said process comprising following steps:

step 1: providing a cell or tissue of a target plant;
step 2: transferring a gene expression cassette containing the inventive promoter sequence (SEQ ID No: 3) into the cell or tissue of a target plant obtained in step 1 to obtain a transgenic plant cell or transgenic plant tissue; and
step 3: culturing the transgenic plant cell or transgenic plant tissue obtained in step 2 to produce a transgenic plant or part of organ, tissue or cell thereof comprising the gene expression cassette containing the inventive promoter sequence (SEQ ID No: 3).

wherein the gene transfer described in said step 2 includes, but not limited to: *Agrobacterium tumefaciens* mediation, recombinant virus transformation, transposon vector transfer, gene gun, electroporation, micro-injection, pollen tube pathway, liposome-mediation, ultrasonic-mediation transfer, silicon carbide fiber-mediated transformation, electrophoresis, laser microbeam mediation, polyethylene glycol (PEG) mediation, calcium phosphate-mediated transformation, DEAE-dextran transformation and the like.

These features and advantages of the present invention will be fully understood and appreciated from the following detailed description of the accompanying Drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 shows the expression analysis of reporter gene β-glucuronidase (GUS) in various tissue of the progeny of *Arabidopsis thialana* transformant containing pMhUBQ1p:: GUS-NOS gene expression cassette.

FIG. 5 shows expression analysis results of reporter gene β-glucuronidase (GUS) at various tissue of *Nicotiana tabacum* L. transformant progeny comprising MhUBQ1p:: GUS-NOS gene expression cassette.

DETAILED DESCRIPTION OF THE PREFERRED EMBODIMENT

Example 1

Figure 1A:
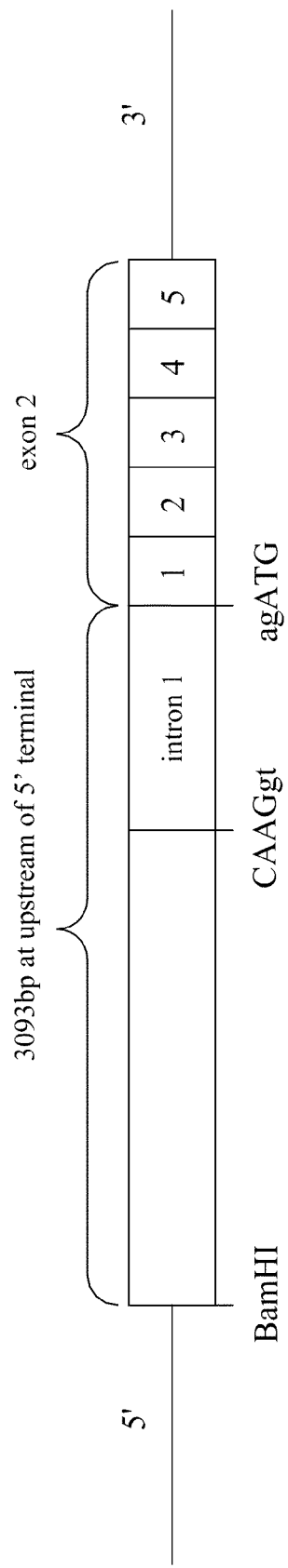
FIG. 1A is the genomic restriction map of the inventive banana polyubiquitin gene MhUBQ1.

Cloning of Banana Polyubiquitin Gene Mh-UBQ1 Promoter

1. Sources of Banana λEMBL3 Genomic Library (Genomic Library)

Banana genomic library was genomic DNA that was extracted from leaves of a banana species, *Musa* spp. cv. Hsien Jin Chiao (AAA group) plant, and the genomic library was constructed then by cleavage substitution of DNA fragments using bacteriophage λEMBL3 as the vector.

2. Preparation and Labeling of Nucleic Acid Probe

Nucleic acid probe was prepared by using a gene fragment of *Arabidopsis thialana* polyubiquitin UBQ3 gene (GeneBank accession number L05363, SEQ ID No: 1) as the template, and employing Prime-A-Gene kit (Promega, USA) in the process described below: total reaction volume was 50 µL, consisting of 1× labeling buffer, pH 6.6 {50 mM Tris-HCL, pH 8.3, 5 mM $MgCl_2$, 2 mM DTT, 0.2 M HEPES [N-(2-hydroxyethyl)piperazine-N'-(2-ethanesulfonic acid)], 26$A_{260}$ unit/mL random hexadeoxyribonicleotides}, 20 µM each of dATP, dGTP, and dTTP, 500 ng/mL denatured DNA template, 400 µg/mL Bovine serum albumin (BSA), 50 µCi [$\alpha$-$^{32}$P] dCTP (333 nM), and 5 unit Klenow DNA Polymerase. The reaction was carried out at 37° C. for 2 hours, and then 2 µL of 0.5 M EDTA (pH 8.0) was added to terminate the reaction. Thereafter, 8 µL of tracking staining agent (50% glycerol, 0.25% bromophenol blue) was added. The reaction solution was passed through Sephadex-G50 chromatographic column, and was eluted with TE (pH 7.6) buffer solution; every 160-180 µL aliquot was collected in a tube. Radioactivities of these aliquots were determined in a scintillation counter (Liquid Scintillation Counter, Beckman 1801) and the aliquot with the highest radioactivity was used as the probe.

3. Selection of Banana Polyubiquitin Gene Mh-UBQ1 Genomic Library

Banana genomic library was selected by plaque hybridization. At first, E. coli strain XL1-Blue MRA (P2) used as the infiltration host of λEMBL3 was cultured in NZY medium (consisting of 5 g NaCl, 2 g $MgSO_4.7H_2O$, 5 g yeast extract per liter). 1.5 million plaque forming units were selected under high stringency.

Bacteriophages were transferred on a nitrocellulose membrane, and the membrane thus transferred was treated in a denaturing buffer (0.5 M NaOH, 1.5 M NaCl) for 2 minutes, then in a neutralization buffer [0.5 M Tris base, 1.5 M NaCl, 0.035% HCl (v/v)] for 5 minutes, and finally incubated in 2×SSPE (1×SSPE, consisting of 0.18 M NaCl, 10 mM $NaH_2PO_4$, 1 mM EDTA pH7.4) for 30 seconds. Thereafter, the membrane was treated in a vacuum oven at 80° C. for 2 hours to immobilize bacteriophage DNA and then was incubated in a solution containing 2×SSPE and 0.1% SDS. The mixture was shaken at room temperature for one hour. Then, the nitrocellulose membrane was transferred in a pre-hybridization solution containing 5×SSPE, 5×BFP (1×BFP consisting of 0.02% BSA, 0.02% Ficoll-400000, 0.02% PVP-360000), 0.1% SDS, 50% formamide and 500 µg/mL salmon sperm DNA. A pre-hybridization reaction was carried out at 37° C. for 2 hours. Next, a hybridization reaction was carried out on the membrane with a radio-labeled probe in 5×SSPE, 1×BFP, 0.1% SDS, 50% formamide and 100 µg/mL salmon sperm DNA at 37° C. for 16~18 hours. Thereafter, the nitrocellulose membrane was treated twice in a wash buffer I (5×SSPE, 0.1% SDS) at room temperature for 15 minutes, then twice in a wash buffer II (1×SSPE, 0.5% SDS) at 37° C. for 15 minutes to remove non-specific probes. After developing by pressing exposure on an X-film (Kodak XAR film) at −80° C., bacteriophages containing target gene DNA could be detected. Said bacteriophages were isolated from the medium, stored in a SM buffer solution containing 0.03% chloroform. After several purifications, a banana polyubiquitin gene Mh-UBQ1 genomic clone λMhUBQ79 was obtained.

4. Extraction of λMhUBQ79 Bacteriophage Clone DNA

The thus-obtained liquor containing bacteriophages clone λMhUBQ79 was placed on NZY solid medium. The bacteriophage liquor was grooved with a toothpick, and then 3 mL Top agar containing host cells E. coli XL1-Blue MRA (P2) was added, and mixture was cultivated on NZY solid medium at 37° C. for 8 hours. On the next day, mono-plaque agar plaque was picked up from the groove with a capillary. The plaque was spread and cultivated again over a NZY solid medium at 37° C. for 7~11 hours. Then, the medium was placed in a refrigerator at 4° C. Bacteriophages were lysed by adding SM. The lysate was collected in a centrifuge tube, and chloroform was added to 0.03%, and then was centrifuged at 4° C. and 7,000 rpm (Beckman J2-MC, JS-13.1) for 5 minutes. It was stored at 4° C. for use. Thereafter, the target bacteriophage clone mass reproduced above was used to infect host cells at a bacteria ratio of 5:1 as follow: 1 mL SM buffer solution and 5 mL of 2.5 mM $CaCl_2$ was added, well-mixed, stored at room temperature for 15 minutes and then at 37° C. for 45 minutes. Then, it was poured in 100 mL 2×NZY liquid medium (0.4% $MgSO_4 \cdot 7H_2O$, 2% NaCl, 1% bacto-yeast extract, 2% NZ amine, 0.2% casamino acid, 5 mM $MgSO_4$, 25 mM Tris-HCl pH7.5), and was cultured at 37° C. and 240 rpm for more than 8 hours. 4.5 mL chloroform was added, and the mixture was treated by shaking at 37° C. and 240 rpm for 15 minutes, and then the mixture was centrifuged at 4° C. and 7,000 rpm for 20 minutes (Beckman J2-MC, JA 10 rotor). To the supernatant, 100 µL DNase I (1 mg/mL) and 100 µL RNaseA (10 mg/mL) were added. The mixture was treated at 37° C. and 80 rpm for 45. 33 mL of 4M NaCl was added thereto, and the mixture was cooled in an ice bath for 1 hour. Then, 33 mL ice-cold 50% polyethylene glycol was added thereto, and was settled at 4° C. overnight. The mixture was centrifuged at 4° C. and 5,000 rpm for 20 minutes (Beckman J2-MC, JA 10 rotor). The supernatant was discarded. The pellet was air-dried and then was re-suspended in 500 µL PKB solution (10 mM NaCl, 10 mM Tris-HCl pH 8.0, mM EDTA, 0.1% SDS). Thereafter, proteinase K (final concentration 12.5 µg/mL) was added thereto and reacted at 37° C. for 20 minutes. The mixture was extracted successively with equal volume of phenol, PCI (phenol: chloroform: isoamyl alcohol=25:24:1), CI (chloroform:isoamyl alcohol=24:1) and centrifuged at room temperature and 14,000 rpm for 5 minutes. To the supernatant was added 2-fold volume of −20° C. 100% ethanol, and the mixture was centrifuged at 4° C. and 14,000 rpm for 10 minutes. The supernatant was discarded and the pellet was air-dried. The precipitated DNA washed with 70% ethanol, and 100% ethanol, respectively, then dissolved in TE (pH 7.5) buffer solution, and stored at 4° C. for use.

5. Sequencing of DNA

DNA sequencing was carried out on an automatic nucleic acid sequencer (ABI sequencer 377) to obtain the sequence of the genomic clone λMhUBQ79 of banana polyubiquitin gene Mh-UBQ1, and was analyzed with PC/Gene software from IntelliGenetics Inc. The result was shown in FIG. 1A, where genomic clone λMhUBQ79 of banana polyubiquitin gene Mh-UBQ1 contained 5'upstream region ahead of the translation start site (ATG) and a coding region. Said 5'upstream region comprised the postulated gene promoter, 5' terminal untranslation region (5'UTR), postulated exon 1 and intron 1; wherein the second exon of the coding region is consisted of 5 homogeneous ubiquitin genes aligned head-to-tail repeat in same direction (5 homogeneous ubiquitin genes were designed as 1, 2, 3, 4 and 5, respectively); wherein its translation start site (gene code ATG) was located on the first nucleotide of the exon 2. The inventive banana polyubiquitin gene Mh-UBQ1 promoter was selected from the DNA sequence of about 3,093 bp in the 5' upstream region (5' upstream) of the translation start site (ATG), as shown in SEQ ID No: 3.

Example 2

Figure 1B:
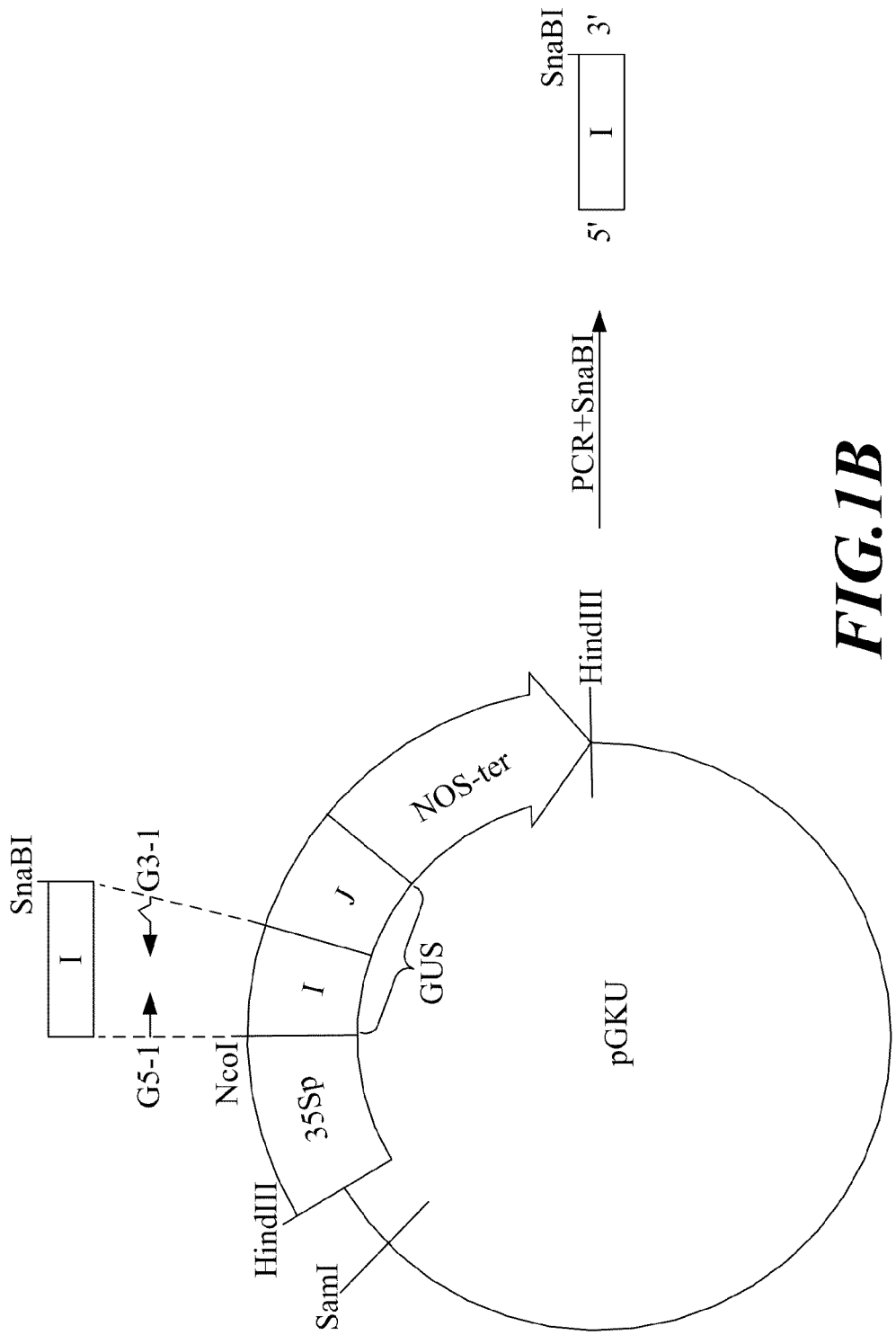
FIG. 1B is a construction strategy scheme for constructing partial GUS fragment (fragment I).
Figure 1C:
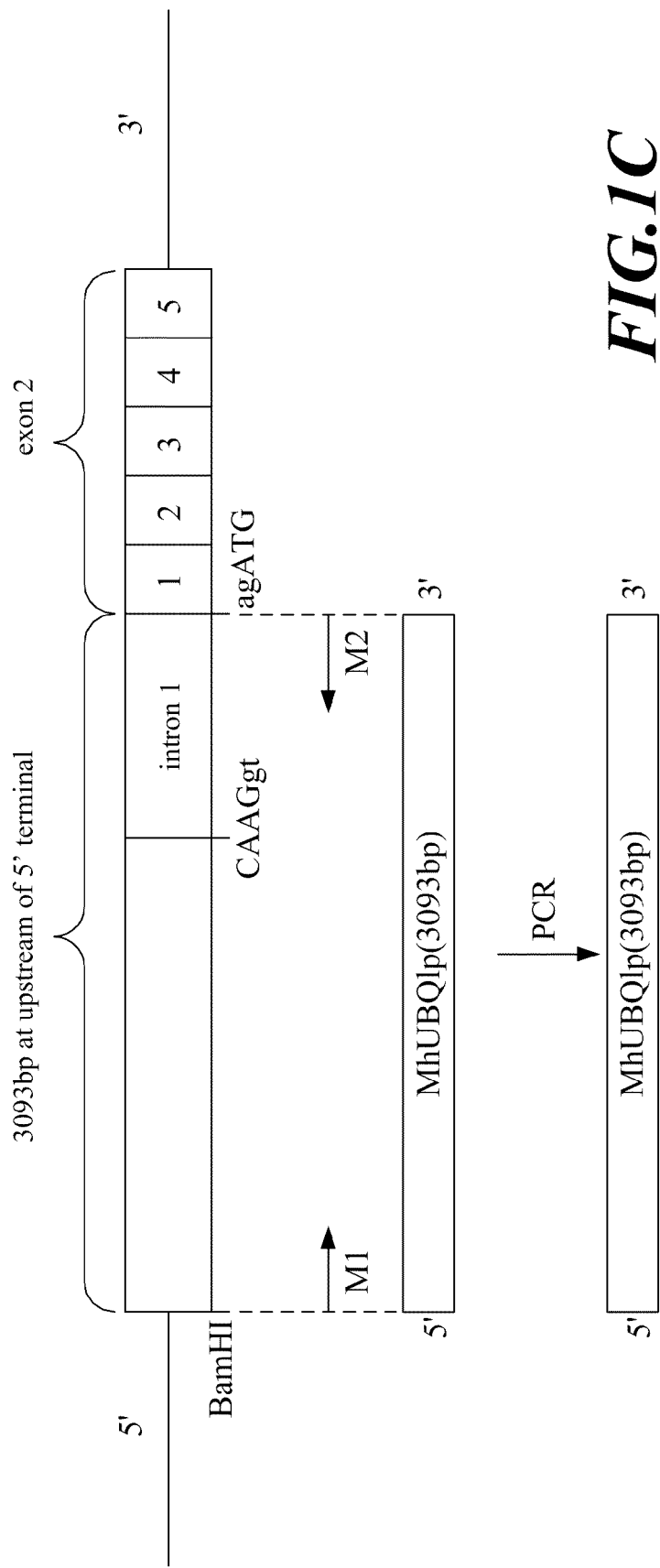
FIG. 1C is a construction strategy for constructing said banana polyubiquitin gene Mh-UBQ1 promoter (MhUBQ1p fragment).
Figure 1D:
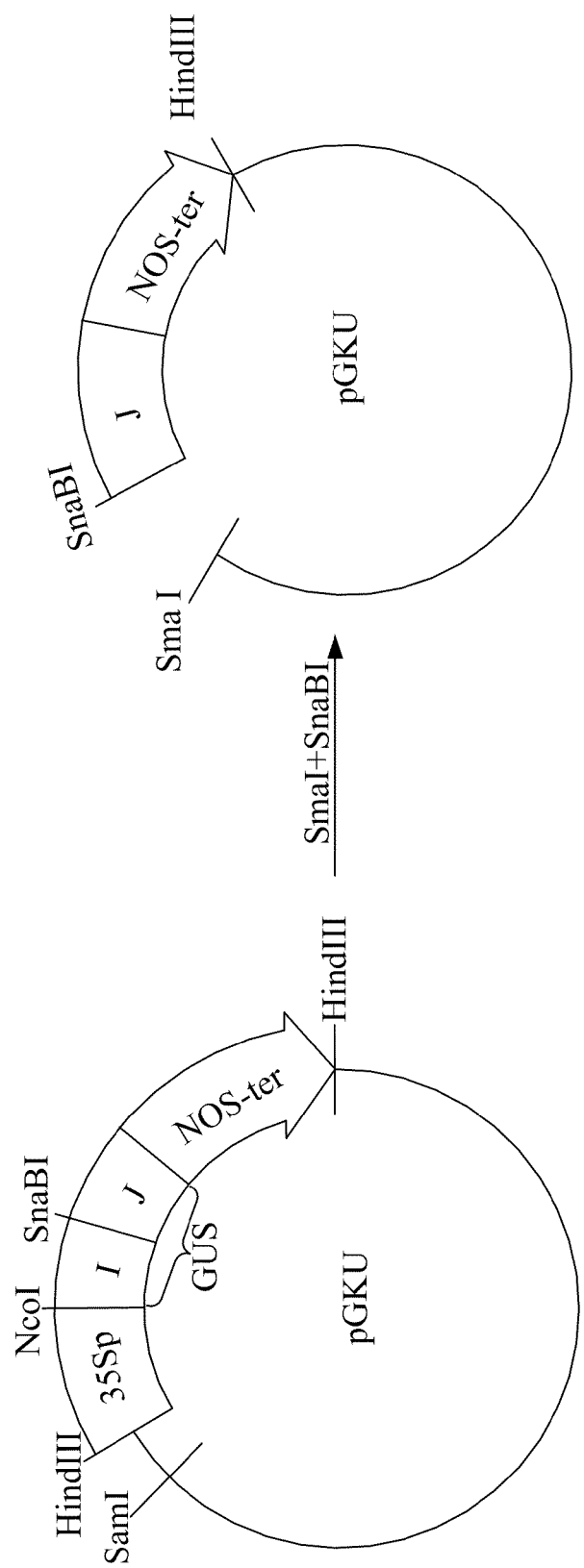
FIG. 1D is a construction strategy scheme for constructing cleaved pGKU.
Figure 1E:
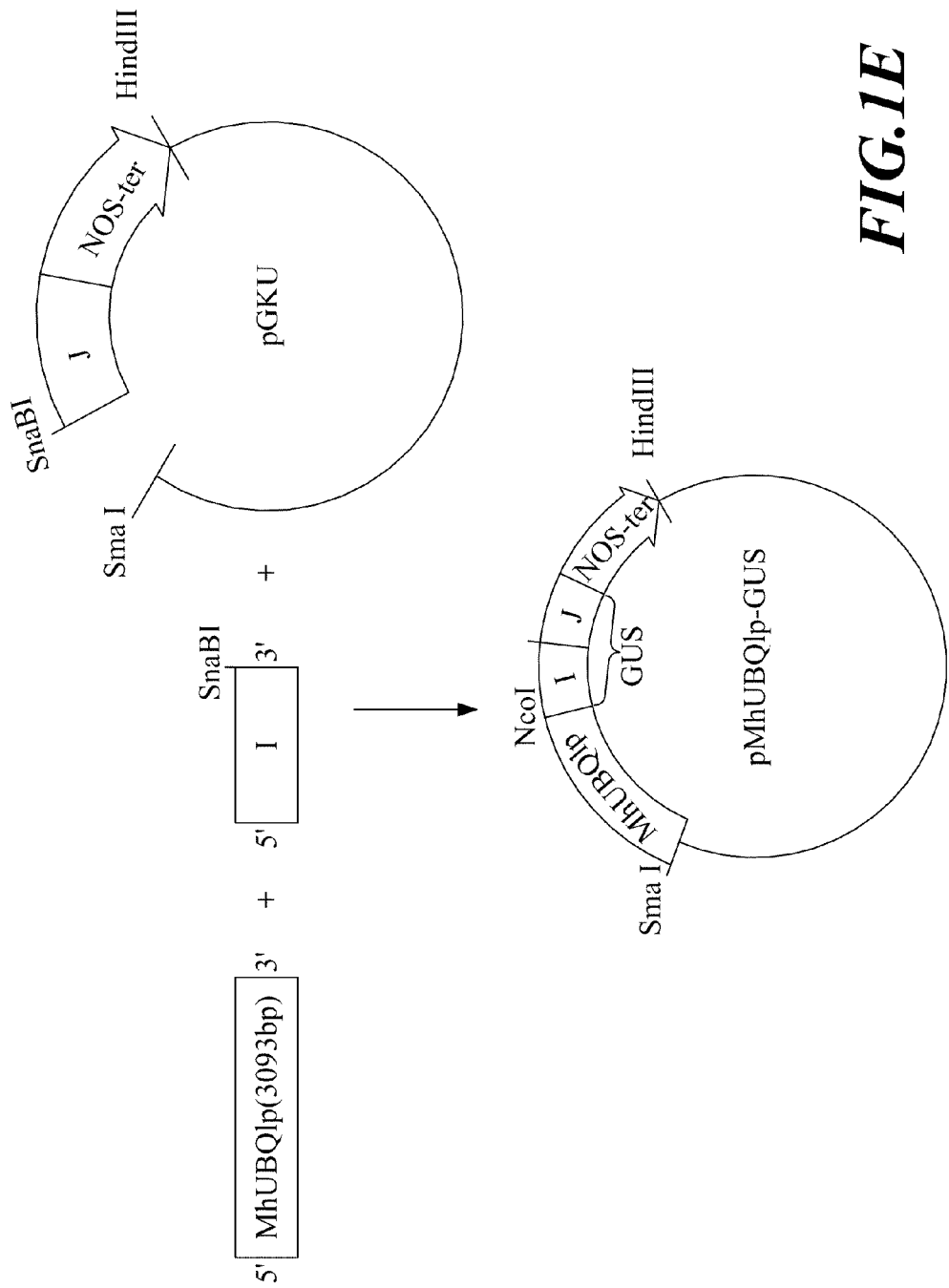
FIG. 1E is a construction strategy for constructing a plasmid pMhUBQ1p-GUS of the inventive banana polyubiquitin gene MhUBQ1 promoter.

Construction of Vector Containing Banana Polyubiquitin Gene Mh-UBQ1 Promoter Construction strategy of banana polyubiquitin gene Mh-UBQ1 promoter was shown in FIG. 1E, where 3,093 bp promoter sequence (SEQ ID No: 3) ahead of translation start site of banana polyubiquitin gene Mh-UBQ1 was constructed into a transformation vector pGKU for *Agrobacterium tumefaciens* to replace the original CaMV 35S promoter (35Sp) in a manner that banana polyubiquitin gene Mh-UBQ1 promoter (SEQ ID No: 3) was ligated to the 5' terminal of reporter gene β-glucuronidase (GUS) gene sequence so as to act as the promoter of said reporter gene.

Step 1: Construction of *Agrobacterium tumefaciens* Transformation Vector pGKU

Figure 2:
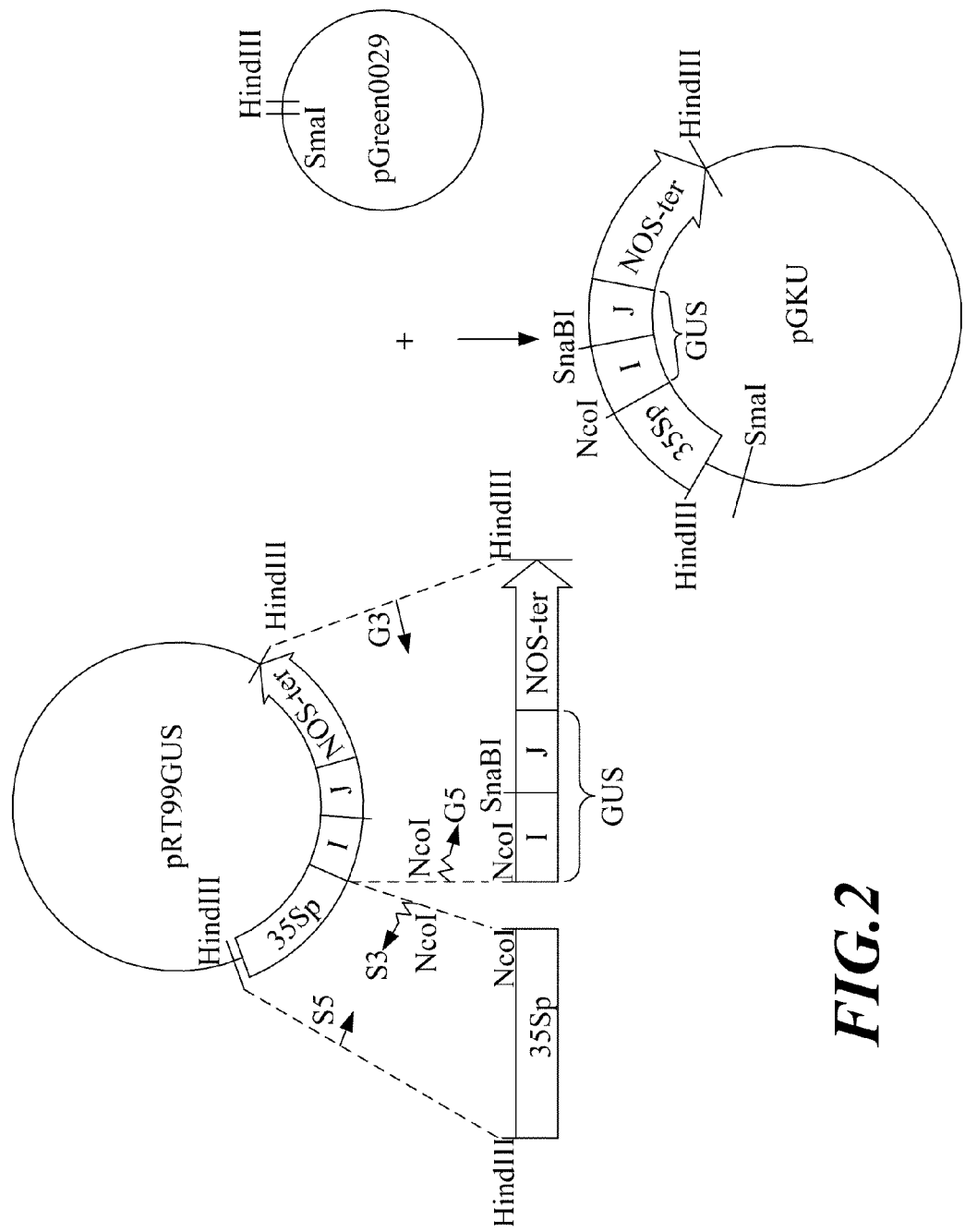
FIG. 2 shows the construction strategy for the transformation vector pGKU of *Agrobacterium tumefaciens*.

The construction strategy for *Agrobacterium tumefaciens* transformation vector pGKU was shown in FIG. 2, where a CaMV 35S promoter (35Sp)-reporter gene (GUS)-terminator (NOS-ter) fragment (CaMV 35s::GUS-NOS) on a commercial vector pRT99GUS was constructed into a commercial *Agrobacterium tumefaciens* transformation vector pGreen0029 (John Innes Centre) so as to obtain an *Agrobacterium tumefaciens* transformation vector pGKU. The construction strategy comprised synthesis of CaMV 35S promoter (35Sp) DNA fragment and reporter gene (GUS)-terminator (NOS-ter) DNA fragment through polymerase chain reaction (PCR), respectively; by means of the design of PCR primer, NcoI restrictive cleavage site was inserted on the 3' terminal of CaMV 35S promoter (35Sp) DNA fragment and the 5'terminal of reporter gene (GUS)-terminator (NOS-ter) DNA fragment, respectively; and finally, these two PCR-derived fragments were constructed in pGreen0029 to obtain *Agrobacterium tumefaciens* transformation vector pGKU.

Step 1.1: Obtaining of CaMV 35S Promoter (35Sp) Fragment on a Commercial Vector pRT99GUS By using DNA of a commercial vector pRT99GUS as a template, amplification of DNA sequence of CaMV 35S promoter (35Sp) fragment was carried out through PCR, where PCR used primers with following sequences:

```
forward primer S5 (containing HindIII
restriction site):
                                       (SEQ ID No: 4)
 5'-tgcatgcatgcaagcttg-3'
                  HindIII reverse primer S3 (containing NcoI restriction
site):
                                       (SEQ ID No: 5)
 5'-ataccatggcccggggatcctctagagtcgaggtcct-3'
       NcoI
```

The total reaction volume of PCR was 50 μl (comprising: 1 μl genomic DNA, 10 μl 5× Phusion HF buffer solution, 1 μl 10 mM dNTP, 1 μl 20 μM forward primer, 1 μl 20 μM reverse primer, 35.5 μl sterile water, 0.5 μl Phusion DNA polymerase). PCR reaction conditions were: after reaction at 98° C. for 30 seconds, performing total 35 cycles of: reactions at 98° C. for 10 seconds, 60° C. 30 seconds, and 72° C. 60 seconds, and finally, reaction at 72° C. for 10 minutes as elongation. A PCR product of 544 bp in length was synthesized. The PCR product was cleaved with HindIII and NcoI restrictive enzymes to recover a DNA fragment of 470 bp in length (fragment S) which was stored at 4° C. for use.

Step 1.2: Obtaining Reporter Gene (GUS)-Terminator (NOS-Ter) Fragment on a Commercial Vector pRT99GUS Similarly, DNA sequence of a commercial vector pRT99GUS was used as a template, and an amplification of DNA sequence of reporter gene (GUS)-terminator (NOS-ter) fragment was carried out by polymerase chain reaction (PCR). Primers used in PCR had following sequences:

```
forward primer G5 (containing NcoI restriction
site):
                                       (SEQ ID No: 6)
 5'-ataccatggtacgtcctgtag-3'
       NcoI reverse primer G3 (containing HindIII restriction
site):
                                       (SEQ ID No: 7)
 5'-acggccagtgccaagcttgcat-3'
                 HindIII
```

Total reaction volume of PCR was 50 μl (comprising: 1 μl genomic DNA, 10 μl of 5× Phusion HF buffer solution, 1 μl of 10 mM dNTP, 1 μl of 20 μM forward primer, 1 μl of 20 μM reverse primer, 35.5 μl sterile water, 0.5 μl Phusion DNA polymerase). PCR reaction conditions were: after reaction at 98° C. for 30 seconds, performing total 35 cycles of reactions at 98° C. for 10 seconds, 60° C. 30 seconds, and 72° C. 60 seconds, and finally, reaction at 72° C. for 10 minutes as elongation. A PCR product of 2,108 bp in length was synthesized. PCR product was cleaved with HindIII and NcoI restriction enzymes, and a DNA fragment (fragment G) of 2,093 bp in length was recovered and stored at 4° C. for use.

Step 1.3: DNA Ligation

A commercial vector pGreen0029 was cleaved with HindIII restriction enzyme, a DNA fragment (fragment P) of 4,632 bp in length was recovered, and DNA ligations were carried out with fragment S and fragment G obtained separately from the above steps 1.1 and 1.2 to obtain *Agrobacterium tumefaciens* transformation vector pGKU. As shown in FIG. 2, in addition to the feature of pGreen, said *Agrobacterium tumefaciens* transformation vector pGKU possessed CaMV 35S promoter (35Sp)-reporter gene (GUS)-terminator (NOS-ter) DNA fragment of a commercial vector pRT99GUS, as well as it had a NcoI restriction site at the 3'terminal of the CaMV 35S promoter (35Sp). Accordingly, *Agrobacterium tumefaciens* transformation vector pGKU could utilize the multiple cloning site comprising SmaI restriction site in pGreen0029, and NcoI restriction site to replace CaMV 35S promoter (35Sp) with other promoter sequence so as to initiate reporter gene GUS.

Step 2: Obtaining of Partial Sequence of GUS Fragment

For maintaining the self-splicing function (i.e., following ag/GT principle) of intron 1 in banana polyubiquitin gene thus constructed in order to assure the high activating ability of the promoter, NcoI restriction site of *Agrobacterium tumefaciens* transformation vector pGKU was not used but in stead, each insert fragment was prepared through PCR, as shown in FIG. 1B. By using *Agrobacterium tumefaciens* transformation vector pGKU as the template, a partial GUS fragment from GUS translation start site (ATG) to SnaBI restrictive site was synthesized at first by amplification through PCR. Primers used in PCR had following sequences:

```
forward primer G5-1:
                                       (SEQ ID No: 8)
 5'-atggtacgtcctgtagaaacc-3' reverse primer G3-1 (containing SnaBI restriction
site):
                                       (SEQ ID No: 9)
 5'-tgatacgtacacttttcccggc-3'
       SnaBI
```

Total reaction volume of PCR was 50 μl (comprising: 1 μl genomic DNA, 10 μl 5×Phusion HF buffer solution, 1 μl of 10 mM dNTP, 1 μl of 20 μM forward primer, 1 μl of 20 μM reverse primer, 35.5 μl sterile water, 0.5 μl Phusion DNA polymerase). PCR reaction conditions were: after reaction at 98° C. for 30 seconds, performing total 35 cycles of reactions at 98° C. for 10 seconds, 60° C. 30 seconds, and 72° C. 60 seconds, and finally, reaction at 72° C. for 10 minutes as elongation. PCR product was cleaved with SnaBI restriction enzyme, a partial GUS fragment (fragment I) of 387 bp in length was recovered and stored at 4° C. for use.

Step 3: Obtaining Banana Polyubiquitin Gene Mh-UBQ1 Promoter (MhUBQ1p) Sequence

Banana genomic DNA extracted as described in Example 1 was used as template, amplification of the sequence of 3,093 bp (SEQ ID No: 3) ahead of the translation start site of banana polyubiquitin gene Mh-UBQ1 promoter was carried out by polymerase chain reaction (PCR), as shown in FIG. 1C.

Primers used in the PCR had following sequences:

```
forward primer M1:
5'-ggatccacatgttctgcagatagatag-3'    (SEQ ID No: 10)

reverse primer M2:
5'-ctgatcaaagagataaaagaagaaagg-3'    (SEQ ID No: 11)
```

Total reaction volume of PCR was 50 μl (comprising: 1 μl genomic DNA, 10 μl 5×Phusion HF buffer solution, 1 μl of 10 mM dNTP, 1 μl of 20 μM forward primer, 1 μl of 20 μM reverse primer, 35.5 μl sterile water, 0.5 μl Phusion DNA polymerase). PCR reaction conditions were: after reaction at 98° C. for 30 seconds, performing total of 35 cycles of: 98° C. 10 seconds, 65° C. 30 seconds, and 72° C. 60 seconds, and finally, 72° C. for 10 minutes as elongation. PCR product (fragment MhUBQ1p) of full length was recovered and stored at 4° C. for use.

Step 4: DNA Ligation

The *Agrobacterium tumefaciens* transformation vector pGKU prepared in step 1 was cleaved with SmaI+SnaBI double restriction enzymes (as shown in FIG. 1D), and after purification, a cleaved pGKU vector was obtained.

Referring to FIG. 1E, this cleaved pGKU vector was ligated with the partial GUS DNA fragment (fragment I) prepared in the step 2 and the banana polyubiquitin gene MhUBQ1 promoter (fragment MhUBQ1p, SEQ ID No: 3) prepared in the step 3 to obtain a plasmid pMhUBQ1p-GUS containing banana polyubiquitin gene MhUBQ1 promoter sequence (SEQ ID No: 3). In said pMhUBQ1p-GUS plasmid, the 3'terminal of the banana polyubiquitin gene MhUBQ1 promoter was ligated with DNA sequence (MhUBQ1p::GUS-NOS) of the reporter gene β-glucuronidase (GUS). Consequently, by transferring said pMhUBQ1p-GUS plasmid into a plant body through *Agrobacterium tumefaciens* transformation, the pattern as banana polyubiquitin gene MhUBQ1 promoter initiating the expression of reporter gene β-glucuronidase (GUS) gene could be analyzed.

Example 3

Analysis of the Transient Expression of Banana Polyubiquitin Gene Promoter with Gene Gun 1. Preparation of Micro-Particle and DNA Packaging To 60 mg of metal tungsten particle with a diameter of 1.7 μm, 1 mL of 70% EtOH was added and after shaking for 3-5 minutes, the mixture was allowed to stand for 15 minutes. After a short centrifuge to settle the particles, the supernatant was discarded. 1 mL sterile water was added thereto, shaken for 1 minute, short centrifuged again, and discarded the supernatant. These treatments were repeated several times. Finally, 1 mL sterile 50% glycerol was added thereto. To 50 μg glycerol suspension containing metal micro-particles, 5 μL plasmid DNA (1 μg/μL), 50 μL of 2.5 M CaCl$_2$, 20 μL of 0.1 M spermidine were added successively, and the mixture was vortexed for 2-3 minutes. The mixture was allowed to stand for 1 minute. After settling by centrifuge, the supernatant was discarded. After washed with 140 μL 70% EtOH and 100% EtOH, respectively, the supernatant was aspirated off, and finally, 48 μL of 100% EtOH was added thereto, and the mixture was stored for use. Each gun hit used 6 μL.

2. Conditions for Gene Gun Transformation

Banana cell suspension, banana pericarp and Phalaenopsis petal were used as materials and treated with pressure-accelerated particle gene gun, PDS-1000/He particle gun, from Bio-Rad under conditions: Gap: ⅜ inches; micro-carrier flight distance: 8 mm; vacuum: 25 inches-Hg; pressure sheets used: 900, 1350 and 1100 Psi, respectively; and distance from material to stop screen: 6 cm.

3. GUS Histochemical Staining

Materials to be tested were incubated in pre-treatment buffer solution [50 mM Na$_3$PO$_4$ (pH6.8), 1% TritonX-100] at 37° C. for 2 hours, and then rinsed 2-3 times with buffer solution (50 mM Na$_3$PO$_4$, pH6.8) containing no Triton X-100. Thereafter, buffer solution (1 mM X-Gluc dissolved in 50 mM Na$_3$PO$_4$, pH 6.8) containing X-Gluc (5-Bromo-4-chloro-3-indoxyl-beta-D-glucuronic acid) was added thereto. The mixture was evacuated at 25 inches-Hg for 5 minutes, and then returned to atmospheric pressure for 5 minutes. This process was repeated once more. The mixture was then placed at 37° C., reacted for 2 days, and finally, 70% ethanol was added to terminate and reaction and tissue discoloration, where coloration was to be observed.

Figure 3:
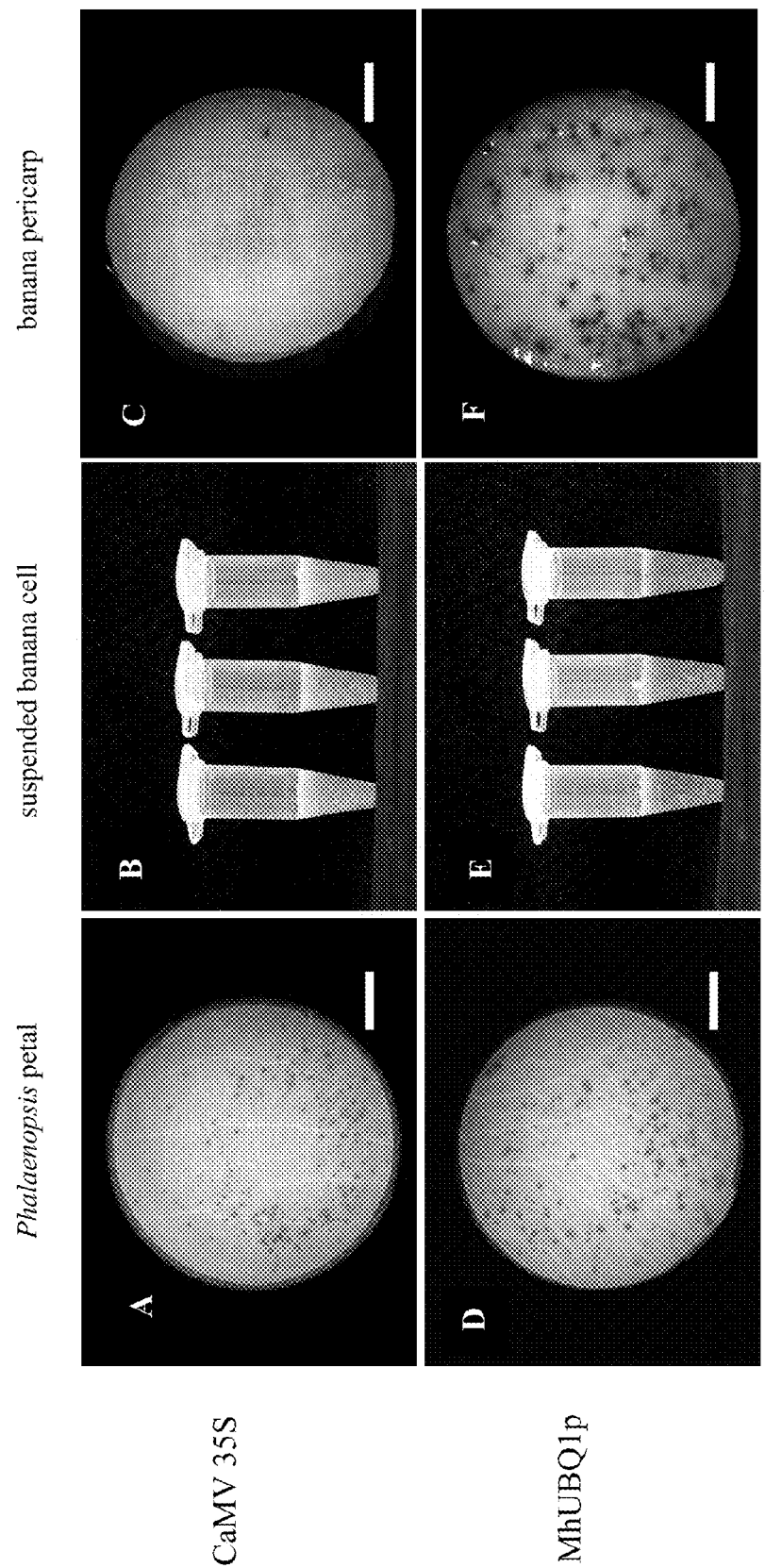
FIG. 3 shows the transient expression of GUS by gene gun transformed said expression vector (pMhUBQ1p-GUS); wherein the materials are *Phalaenopsis* petal, suspended banana cell and banana pericarp, respectively, and the transient expression of CaMV 35S promoter expression vector is used as the control group (FIGS. 3A, B, and C); and wherein the transient expression of MhUBQ1 promoter expression vector is used as the test group (FIGS. 3D, E, and F). The white bar on each figure is 0.5 cm in length.

FIG. 3 shows the results of GUS activity analysis, where conventional CaMV 35S promoter was used as the control group (FIGS. 3 A, B, and C); reporter gene GUS activated with banana polyubiquitin gene MhUBQ1 promoter was test groups (FIGS. 3 D, E, and F), wherein reporter gene GUS activated with banana polyubiquitin gene MhUBQ1 promoter, either for suspended banana cell, banana pericarp or Phalaenopsis petal, their transient expressions in monocotyledon plant materials were analyzed as good activation ability (FIGS. 3 D, E, and F), and especially, suspended banana cell and banana pericarp exhibited significant genetic bombardment results (FIGS. 3 E and F). Within banana tissues, CaMV 35S promoter exhibited extreme low activation ability for GUS (FIGS. 3 B and C), where only few cells presented coloration response. In contrast, banana polyubiquitin gene MhUBQ1 promoter exhibited significant activation ability for downstream GUS gene, indicating that banana polyubiquitin gene MhUBQ1 promoter did have high expression ability in monocotyledon plants. Accordingly, if this promoter could be applied in the gene transfer of monocotyledon plants, the development of the biotechnical industry of monocotyledon plants (for example: paddy rice, corn, banana, orchid and the like) should be improved.

Example 4

Gene Transfer of *Arabidopsis thialana* Through *Agrobacterium tumefaciens* Transformation In this example, *Arabidopsis thialana* was used as a model material. By means of *Agrobacterium tumefaciens* floral dip transformation, pMhUBQ1p-GUS plasmid prepared in Example 2 was transferred into *Arabidopsis thialana* so as to change the genomic constitution of the transgenic plant such that the banana polyubiquitin gene MhUBQ1 promoter could activate effectively the expression of reporter gene GUS in the objective transgenic plant and the progeny thereof. In addition, the expression sites of reporter gene GUS on *Arabidopsis thialana* transformant as well as the expression strength of the banana polyubiquitin gene MhUBQ1 promoter were analyzed by means of GUS active histochemical staining.

1. Growth Condition of *Arabidopsis thialana* Plant Material

Seeds of *Arabidopsis thialana* were wet and cold stratified at 4° C. for 2-4 days and sowed then in a medium consisting of peat:Perlite:vermiculite in a ratio of 10:1:1. Cultivation conditions were: 22-25° C., 16 hours light cycle, and 75% relative humidity. After about 4-6 weeks, the plant was pruned. As the rachis had grown to a length of about 3 inches on 4-8 days after pruning, the plant was subjected to transformation.

2. Preparation of *Agrobacterium tumefaciens* Liquor and Infiltration

*Agrobacterium tumefaciens* LBA4404 strain was inoculated in YEB solid medium (0.5% beef extract, 0.1% yeast extract, 0.5% peptone, 0.5% mannitol, 0.05% $MgSO_4$, 1.25% agar, pH 7.5) containing suitable antibiotics (50 μg/ml of kanamycin, 50 μg/ml of ampicillin), and cultivated at 28° C. for 2 days. Then, single colony was picked, inoculated in 20 ml YEB liquid medium containing suitable antibiotics (50 μg/ml of kanamycin, 50 μg/ml of ampicillin) and cultivated by shaking at 28° C. and 240 rpm for 1 day. 5 ml bacteria liquor thus obtained was added in 200 ml YEB liquid medium and cultivated at 28° C. and 240 rpm for 9 hours. The culture suspension was centrifuged at 4° C. and 4,200 rpm for 20 minutes (Beckman J2-MC, JA-10 rotor). The supernatant was discarded, and the pellet was suspended in 20 ml pre-cooled YEB medium. The resulted suspension was centrifuged again at 4° C. and 4,200 rpm for 20 minutes. The pellet was re-suspended in 20 ml pre-cooled YEB medium and was stored at 4° C. till used. *Agrobacterium tumefaciens* transformation was performed by employing frozen-thaw method. 500 μl suspension of *Agrobacterium tumefaciens* to be transformed was well mixed with 1 μg pMhUBQ1p-GUS plasmid DNA prepared in Example 2, and the mixture was treated successively on ice, in liquid nitrogen and at 37° C., each for 5 minutes. The bacteria liquor was then mixed with 1 ml YEB medium and cultivated by shaking at 28° C. and 240 rpm for 3~4 hours. The bacterial liquor was applied over medium containing suitable antibiotics (50 μg/ml of kanamycin, 100 μg/ml rifamycin, and 20 μg/ml streptomycin), and cultivated at 28° C. for 2 days.

*Agrobacterium tumefaciens* that had been transformed to contain plasmid pMhUBQ1p-GUS prepared in example 2 was used to inoculate single colony of the above-described *Agrobacterium tumefaciens* on 5 ml YEB medium (0.5% beef extract, 0.1% yeast extract, 0.5% peptone, 0.5% mannitol, 0.05% $MgSO_4$, pH 7.5) containing suitable antibiotics (50 μg/ml kanamycin, 100 μg/ml rifamycin, and 20 μg/ml streptomycin) and cultivated by shaking at 28° C. and 240 rpm for 2 days. Then, it was poured in 250 ml YEB medium containing suitable antibiotics (50 μg/ml kanamycin, 100 μg/ml rifamycin, 20 μg/ml streptomycin), and cultivated again by shaking at 28° C. and 240 rpm for more than 24 hours. It was then centrifuged at 4° C. and 6,000 rpm for 10 minutes. The supernatant was discarded, and the pellet was suspended in 200 ml infiltration medium (½ MS, 5% sucrose, 0.044 μM ABA, 0.01% Silwet L-77, pH 5.7). *Arabidopsis thialana* plants to be transformed were placed upside down in the *Agrobacterium tumefaciens* suspension, and soaked there for 20 seconds. *Arabidopsis thialana* plants were taken off and kept wet for 24 hours. Seeds could be harvested after about 3~4 weeks.

3. Sowing and Selection of Transformant

The transformed *Arabidopsis thialana* seeds thus-collected was rinsed several times with sterile water, treated with 70% ethanol for 2 minutes, treated with sterile water containing 1% Clorox and 0.1% Tween-20 for 20 minutes, and then rinsed 4-5 times with sterile water for 5 minutes each time. Thereafter, these seeds thus-treated were sown in germinating medium (½MS, 1% sucrose, 0.7% agar, 50 μg/ml of kanamycin, 50 μg/ml of ampicillin) to carry out segregation assay of anti-antibiotic progeny. Homozygote transformant progeny thus obtained could be used in assay of promoter activity.

4. GUS Histochemical Staining

The procedure described in Example 3 was repeated.

Figure 4A:
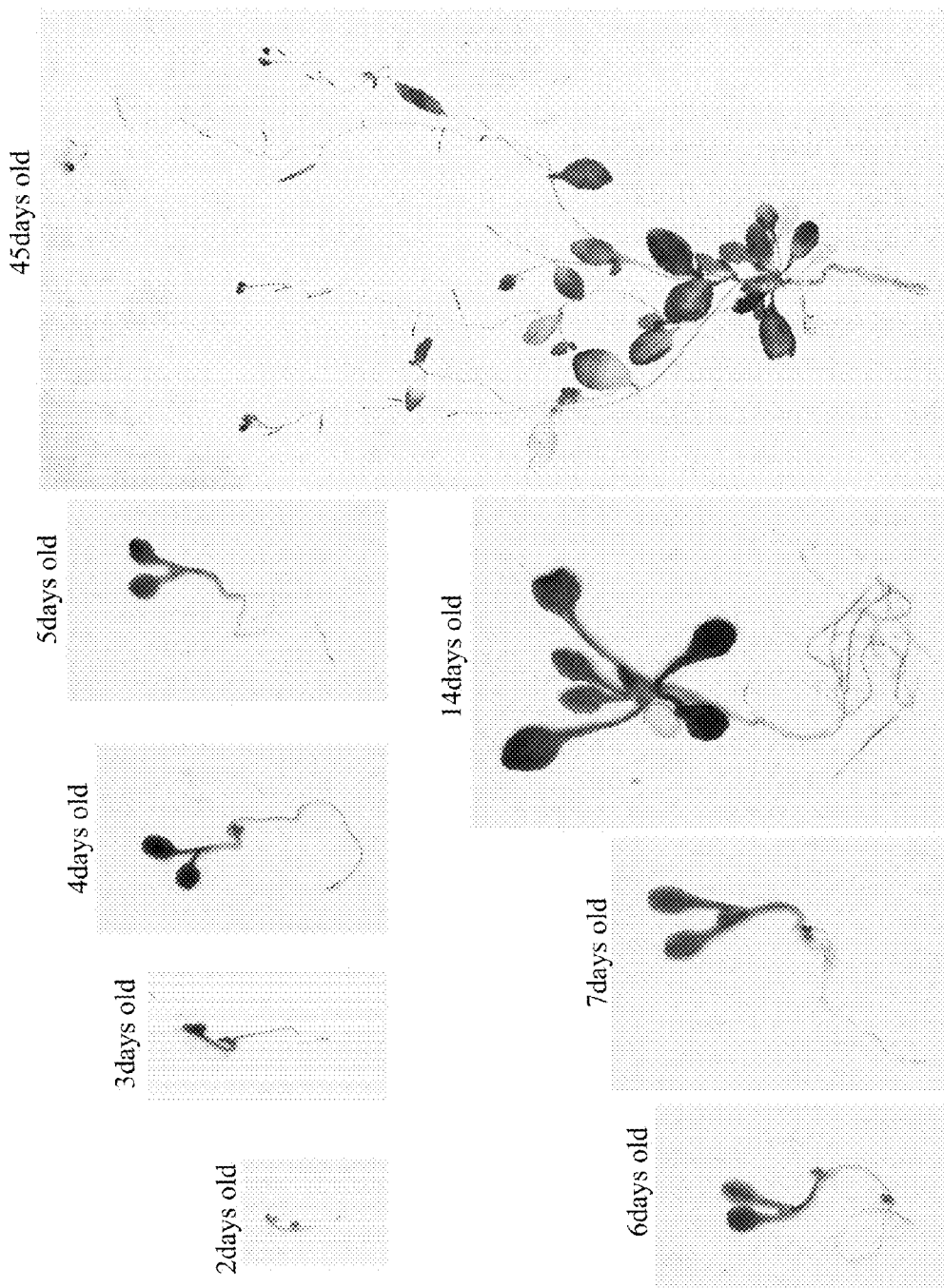
FIG. 4A: GUS histochemical staining results of *Arabidopsis thialana* transformant whole plants grown for different number of days.
Figure 4B:
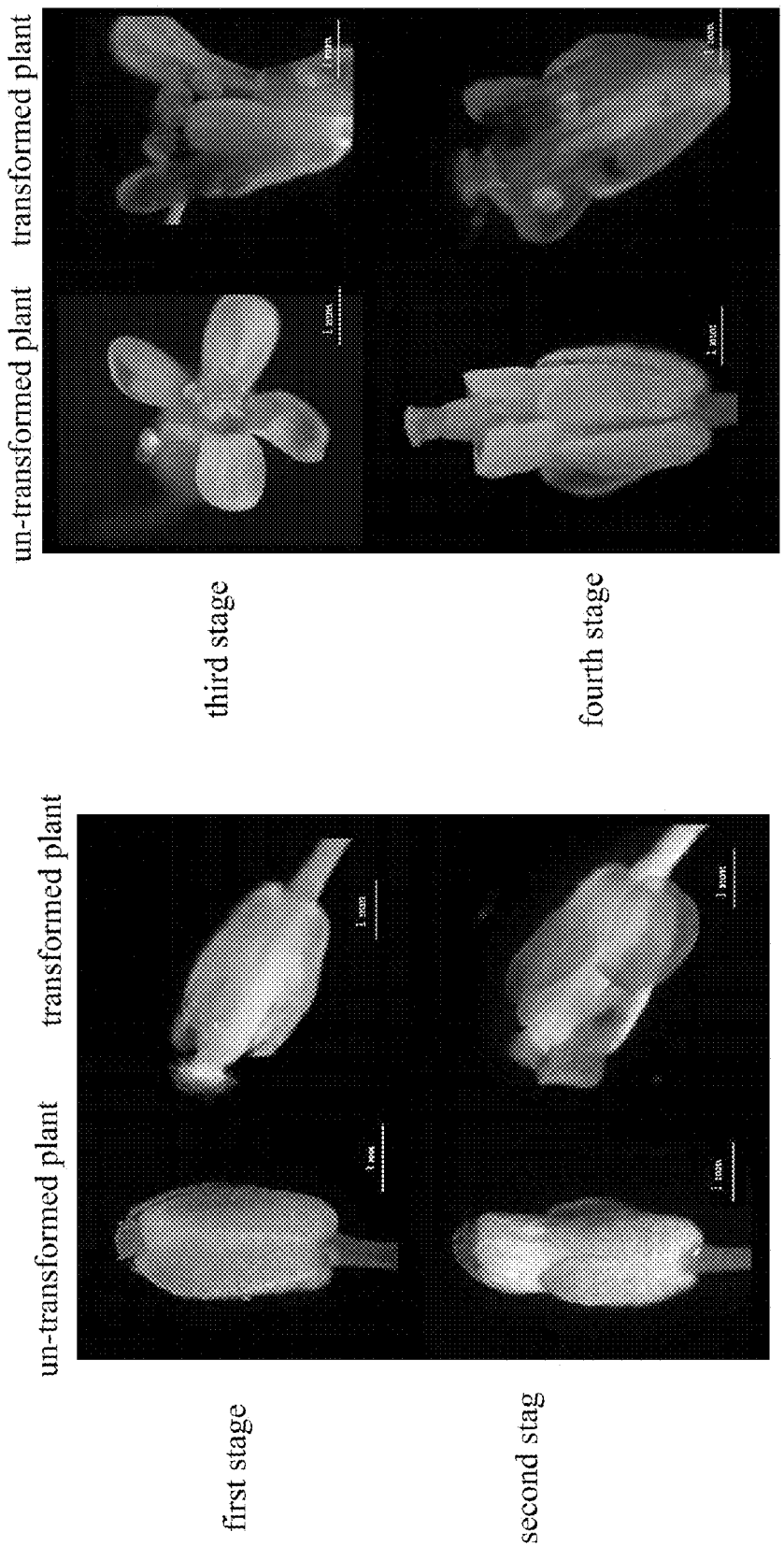
FIG. 4B: GUS histochemical staining results of *Arabidopsis thialana* transformant flower organ at different developmental stages, where non-transformed flower organs at each stage were used as the control groups.
Figure 4C:
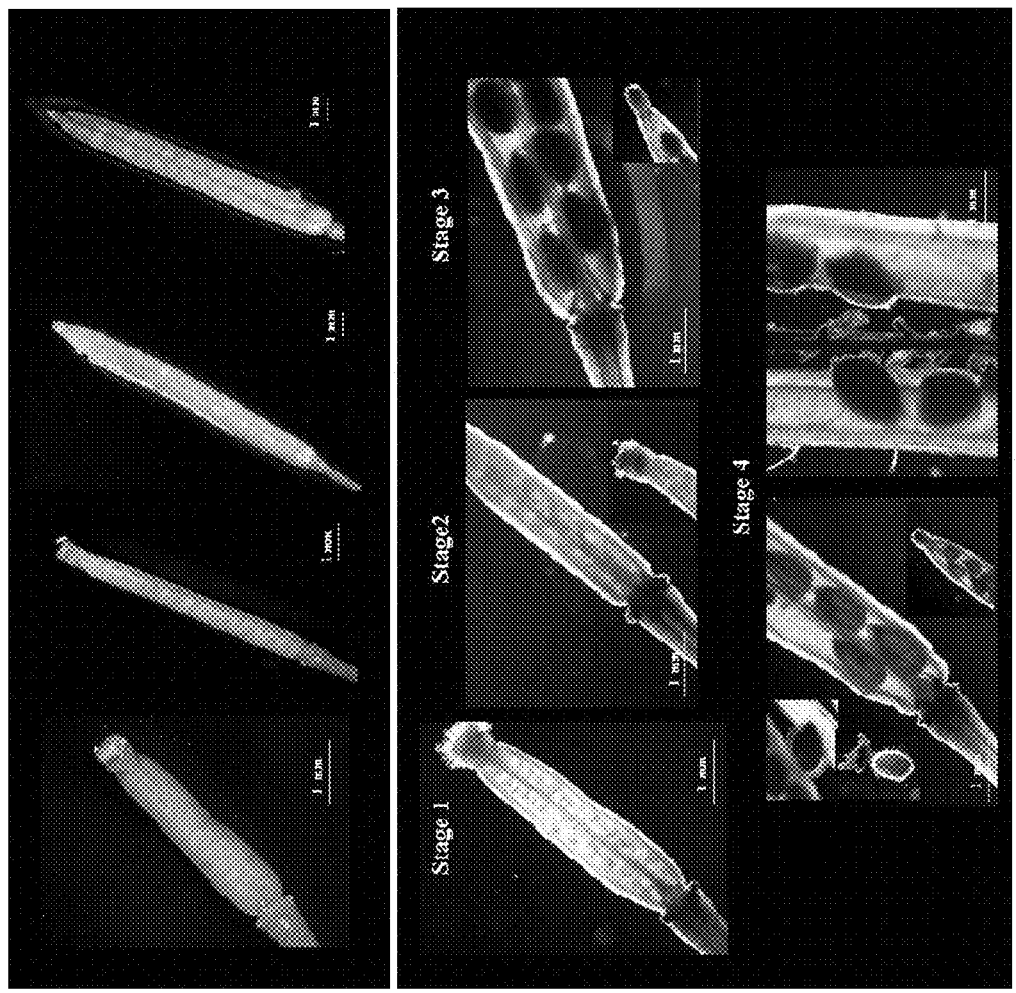
FIG. 4C: GUS histochemical staining results of siliques of *Arabidopsis thialana* transformant at different maturing stages, where non-transformed siliques at different stages were used as the control groups. All transformants tissues assayed presented blue color.

FIG. 4 shows the result of GUS activity analysis. As shown in FIG. 4, reporter gene GUS activated by banana polyubiquitin gene MhUBQ1 promoter could be expressed in every tissue of *Arabidopsis thialana*, including root, stem, leaf, pod and pollinia (as shown in FIG. 4); wherein, FIG. 4A: GUS histochemical staining results of *Arabidopsis thialana* transformant whole plants grown for different number of days; FIG. 4B: GUS histochemical staining results of *Arabidopsis thialana* transformant flower organ at different developmental stages, where non-transformed flower organs at each stage (stages 1-4) were used as the control groups; FIG. 4C: GUS histochemical staining results of siliques of *Arabidopsis thialana* transformant at different developmental stages, where non-transformed siliques at each stage (stage 1-4) were used as the control groups. From results of GUS activity analysis, it indicated that banana polyubiquitin gene MhUBQ1 promoter did have high expression strength, and could be over-expressed in various tissues of the transformant progeny.

Example 5

Transformation of *Nicotiana tabacum* L. via
*Agrobacterium tumefaciens*-Mediated
Transformation Process Separately, *Nicotiana tabacum* L. cv Wisc. 38 was used as the material, and similarly, *Agrobacterium tumefaciens*-mediated transformation was employed to transform plasmid pMhUBQ1p-GUS prepared in Example 2 into *Nicotiana tabacum* L. to alter genomic constitution in the transgenic plant such that banana polyubiquitin gene MhUBQ1 promoter could activate effectively the expression of reporter gene GUS at objective transgenic *Nicotiana tabacum* L. plant and progeny thereof. Furthermore, GUS histochemical staining was used to analyze expression patterns of reporter gene GUS in *Nicotiana tabacum* L. transformant to detect whether banana polyubiquitin gene MhUBQ1 promoter exhibited likewise activation ability with high strength.

1. Preparation of *Agrobacterium tumefaciens* Liquor

The same procedure described in Example 4 was followed in this example.

2. Transformation of *Agrobacterium tumefaciens*

The same procedure described in Example 4 was followed in this example.

3. Small Amount Preparation of Transformed *Agrobacterium tumefaciens* Plasmid

The same procedure described in Example 4 was followed in this example.

4. Transformation and Selection of *Nicotiana tabacum* L.

Leaves of *Nicotiana tabacum* L. cv Wisc. 38 plants sterile seeded were cut into square of 1.5 cm×1.5 cm in a bacteria liquor, placed on N01B1 solid medium (MS, adding 0.1 mg/L of 1-naphthyl acetic acid, 1 mg/L of BA, 3% sucrose, pH 5.7, 0.7% agar) and cultivated at 25° C., 16-hour lighting environment for 3 days. Then, the square leaves were rinsed by dipping in N01B1 liquid medium containing 250 mg/L cefotaxime for 1 minute. Next, they were placed on N01B1 solid medium containing 250 mg/L cefotaxime and 100 mg/L kanamycin, and selected at 25° C., 16-hour lighting environment for 3 weeks. Thereafter, those square leaves were soaked and washed in 20 mL N01B1 liquid medium containing 250 mg/L of cefotaxime for 1 minute. Subsequently, they were transferred on N01B1 solid medium containing 250 mg/L of cefotaxime and 100 mg/L of kanamycin, and were selected at 25° C., 16-hour lighting environment for about 3 weeks. Upon germination of adventitious buds from square leaves, those leaves were moved onto N01B1 solid medium containing 250 mg/l of cefotaxime and 200 mg/l of kanamycin. Selection was carried out at 25° C., 16-hour lighting environment. As shoots had grown to longer than 1 cm, shoots without etiolation could be cut and cottage cultivated in MS solid medium containing 250 mg/L of cefotaxime and 200 mg/L of kanamycin at 25° C. and 16-hour lighting environment till rooting. The plants were used in GUS activity assay.

5. GUS Histochemical Staining

The *Nicotiana tabacum* L. transformant survived in the above selection was subjected to GUS histochemical staining analysis followed the procedure described in example 4.

Figure 5A:
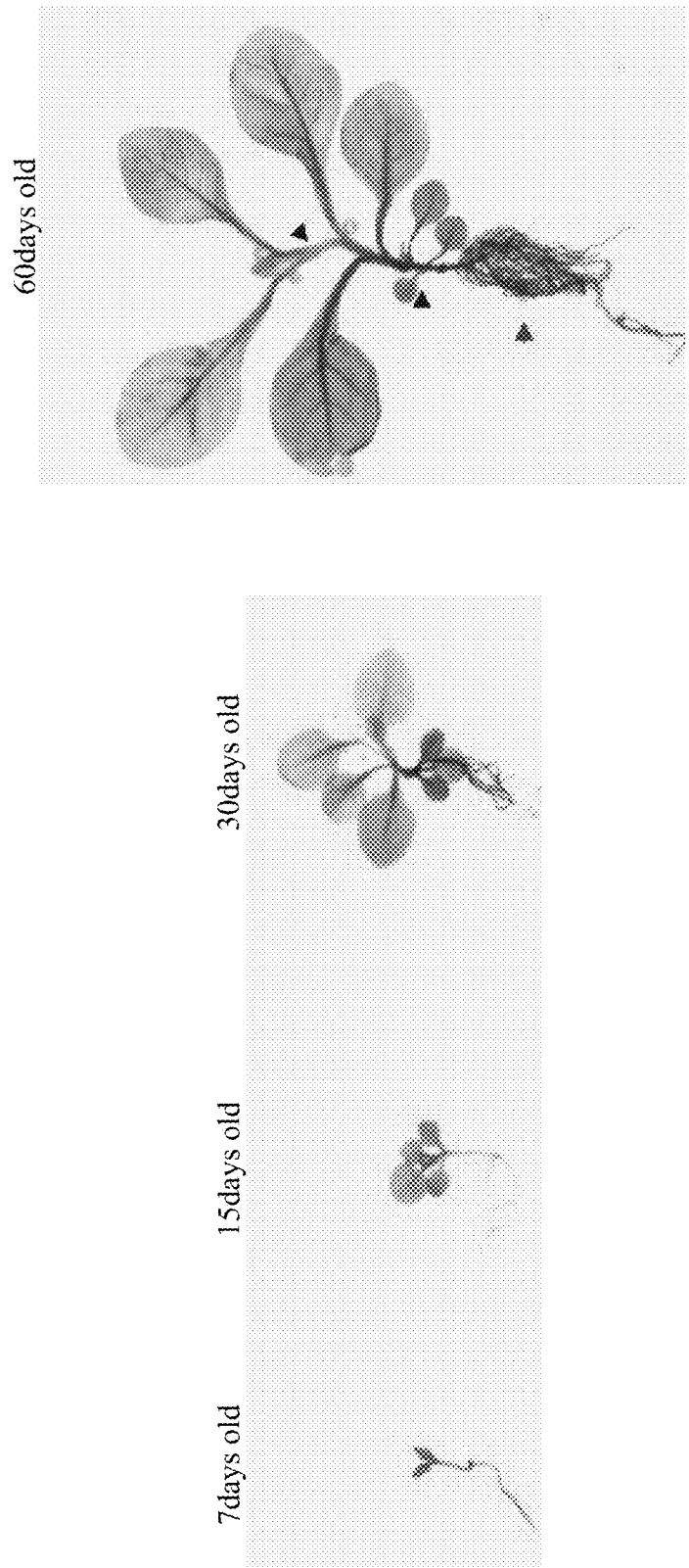
FIG. 5A: GUS histochemical staining results of *Nicotiana tabacum* L. transformant whole plants grown for different number of days.
Figure 5B:
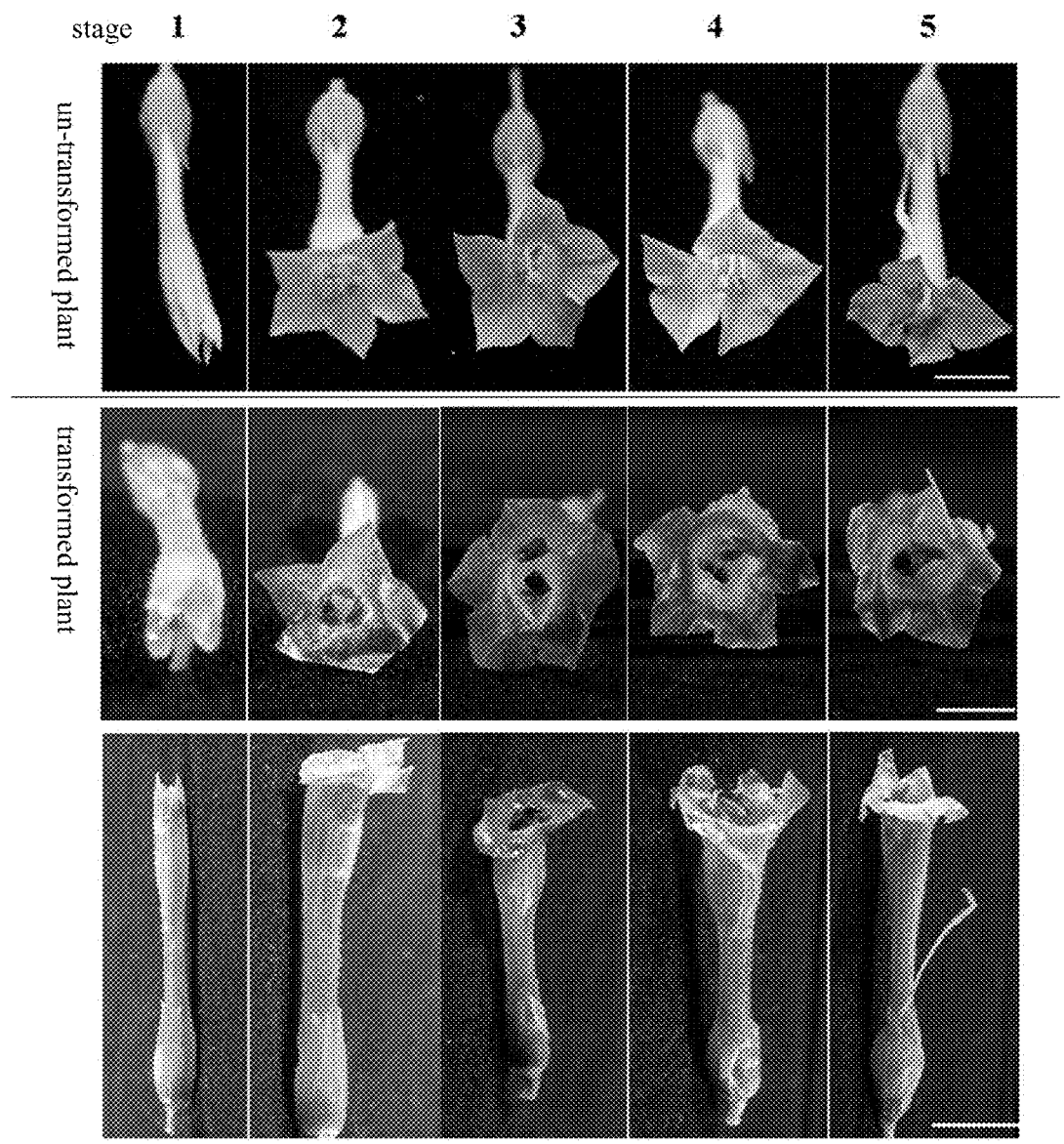
FIG. 5B: GUS histochemical staining results of *Nicotiana tabacum* L. transformant flower organs at different developmental stages, where non-transformed flower organs at different stages were used as control groups. All of the transformant tissues assayed presented blue color.

Results of GUS activity analysis were shown in FIG. 5; wherein FIG. 5A: GUS histochemical staining results of *Nicotiana tabacum* L. transformant whole plants grown for different number of days, and non-transformed flower organs at each stage (stages 1-5) were used as control groups. Here, as shown, reporter gene GUS activated with banana polyubiquitin gene MhUBQ1 promoter could be expressed likewise at all sites of the *Nicotiana tabacum* L. transformant. Accordingly, double analyses of GUS activity in *Arabidopsis thialana* and *Nicotiana tabacum* L. transformants revealed that the inventive banana polyubiquitin gene MhUBQ1 promoter did exhibit significant high expression strength in different spices, as well as could be over-expressed in various tissues of the transgenic plant and progeny thereof.

The promoter that has high expression strength and can be over-expressed in various tissues of a plant as well as its application provided according to the invention has following advantages over other conventional techniques:

1. The inventive promoter can activate the expression of the gene behind its 3'terminal in all tissues of a plant, thereby the high expression strength of said promoter makes possible the over-expression of a target gene in an objective plant so as to increase the product of said target gene.

2. The inventive promoter can be transferred as a vector into a plant, and either a monocotyledon or dicotyledon plants, it exhibits strong activation ability. In a dicotyledon plant, it can be expressed in all sites and tissues, while in monocotyledon plant, its activation ability is higher than that of conventional CaMV 35S promoter; consequently, a common problem as insufficient expression of a transferred gene in a monocotyledon plant can be thus overcome.

While the detailed description provided above is directed to a possible embodiment of invention, it should be understood that said embodiment is not construed to limit the scope of the invention as defined in the appended claims, and those embodiments or alteration that can be made without departing from the spirit and scope of the invention are intended to fall within the scope of the appended claims.

Accordingly, the invention has indeed not only an innovation on the species gene, but also has particularly an expression uniqueness, and therefore, the application should meet sufficiently requirements of patentability on novelty and non-obviousness, and should deserve an invention patent right.

Many changes and modifications in the above described embodiment of the invention can, of course, be carried out without departing from the scope thereof. Accordingly, to promote the progress in science and the useful arts, the invention is disclosed and is intended to be limited only by the scope of the appended claims.

What is claimed is:

1. A promoter that has a high expression strength and can be over-expressed in various tissues of plant, said promoter comprises 5' upstream region ahead of translation start site (ATG), and has the nucleotide sequence of SEQ ID NO: 3.

2. A gene expression cassette, comprising:
the promoter as described in claim 1; and
a polynucleotide having an open reading frame (ORF);
wherein said polynucleotide is linked to the 3' terminal of said promoter, said promoter can activate the transcription of said polynucleotide in an organism containing said gene expression cassette.

3. A gene expression vector, comprising the promoter region as described in claim 1.

4. A plant or a part of organ, tissue or cell of said plant, which, owing to a transformation, has the gene expression cassette as described in claim 2.

5. A process for producing a transgenic plant or a part of organ, tissue or cell thereof containing the gene expression cassette as described in claim 2, comprising the following steps:

step 1: providing a cell or tissue of a target plant;
step 2: transferring the gene expression cassette as described in claim 2 into the cell or tissue of a target plant obtained in step 1 to obtain a transgenic plant cell or transgenic plant tissue; and
step 3: culturing the transgenic plant cell or transgenic plant tissue obtained in step 2 to produce a transgenic plant or part of organ, tissue or cell thereof comprising the gene expression cassette as described in claim 2.

6. The process as recited in claim 5, wherein said transformation described in step 2 comprises one selected from the group consisting of *Agrobacterium tumefaciens* mediation, recombinant virus transformation, transposon vector transfer, gene gun, electroporation, micro-injection, pollen tube pathway, liposome-mediation, ultrasonic-mediation transfer, silicon carbide fiber-mediated transformation, electrophoresis, laser microbeam, polyethylene glycol (PEG) mediation, calcium phosphate-mediated transformation, DEAE-dextran transformation and the like.

* * * * *